(12) United States Patent
Tabatadze et al.

(10) Patent No.: US 11,566,042 B2
(45) Date of Patent: *Jan. 31, 2023

(54) PHOSPHORAMIDITE SYNTHONES FOR THE SYNTHESIS OF SELF-NEUTRALIZING OLIGONUCLEOTIDE COMPOUNDS

(71) Applicant: ZATA Pharmaceuticals, Inc, Worcester, MA (US)

(72) Inventors: David R. Tabatadze, Worcester, MA (US); Ivan B. Yanachkov, Shrewsbury, MA (US)

(73) Assignee: ZATA Pharmaceuticals, Inc, Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/940,039

(22) Filed: Jul. 27, 2020

(65) Prior Publication Data
US 2020/0354397 A1 Nov. 12, 2020

Related U.S. Application Data

(63) Continuation of application No. 15/527,845, filed as application No. PCT/US2015/061343 on Nov. 18, 2015, now Pat. No. 10,723,755.

(Continued)

(51) Int. Cl.
*C07H 21/00* (2006.01)
*C07H 21/02* (2006.01)
(Continued)

(52) U.S. Cl.
CPC ........ *C07H 21/00* (2013.01); *A61K 31/7088* (2013.01); *C07H 19/10* (2013.01);
(Continued)

(58) Field of Classification Search
CPC ........ C07H 21/00; C07H 21/02; C07H 21/04; C07H 19/10; C07H 19/20; A61K 31/7088
See application file for complete search history.

(56) References Cited

U.S. PATENT DOCUMENTS 4,563,307 A * 1/1986 Briden ................. C08K 5/3412
526/263
4,605,698 A 8/1986 Briden
(Continued)

FOREIGN PATENT DOCUMENTS

| CN | 101392108 A | 3/2009 |
|---|---|---|
| WO | 2015073622 A1 | 5/2015 |
| WO | 2016081600 A1 | 5/2016 |

OTHER PUBLICATIONS

Menzi, M. et al., "Polyamine-Oligonucleotide Conjugates: A Promising Direction for Nucleic Acid Tools and Therapeutics", Future Medicinal Chemistry (2015); vol. 7:13, pp. 1733-1749.
(Continued)

*Primary Examiner* — Eric Olson
(74) *Attorney, Agent, or Firm* — Fox Rothschild LLP

(57) ABSTRACT

Compositions and compounds of nucleoside phosphoramidites and modified oligonucleotides, each comprising one or more charge-neutralizing moieties according to the formula V (Continued)

The nucleoside phosphoramidites permit facile attachment of the neutralizing moieties on the backbones of the modified oligonucleotides. The modified oligonucleotides can be used as therapeutic agents (i.e., oligotherapeutics) for the treatment of cancer, autoimmune disorders, genetic diseases, infectious diseases, neurological diseases, inflammatory diseases, metabolic diseases and others.

10 Claims, 19 Drawing Sheets

Specification includes a Sequence Listing.

Related U.S. Application Data

(60) Provisional application No. 62/081,316, filed on Nov. 18, 2014.

(51) Int. Cl.
  *C07H 21/04* (2006.01)
  *C07H 19/10* (2006.01)
  *C07H 19/20* (2006.01)
  *A61K 31/7088* (2006.01)

(52) U.S. Cl.
  CPC ............ *C07H 19/20* (2013.01); *C07H 21/02* (2013.01); *C07H 21/04* (2013.01)

(56) References Cited

U.S. PATENT DOCUMENTS

| | | | | |
|---|---|---|---|---|
| 5,391,785 A * | 2/1995 | Jones | ............... | C07C 323/12 |
| | | | | 536/25.32 |
| 5,612,320 A | 3/1997 | Wurtman et al. | | |
| 5,612,329 A | 3/1997 | Callery et al. | | |
| 5,760,014 A * | 6/1998 | Wurtman | ............... | A61P 15/00 |
| | | | | 514/59 |
| 5,906,996 A * | 5/1999 | Murphy | ............... | A61P 25/28 |
| | | | | 514/674 |
| 6,576,672 B1 * | 6/2003 | Murphy | ............... | A61K 31/13 |
| | | | | 514/183 |
| 7,205,399 B1 | 4/2007 | Vargeese et al. | | |
| 7,314,959 B2 * | 1/2008 | Fahl | ............... | C07C 215/18 |
| | | | | 564/500 |
| 8,642,602 B2 * | 2/2014 | Mann | ............... | A61P 19/04 |
| | | | | 514/393 |
| 9,885,082 B2 * | 2/2018 | Hrdlicka | ............... | C07H 21/00 |
| 10,723,755 B2 * | 7/2020 | Tabatadze | ............... | C07H 21/04 |
| 2005/0074743 A1 | 4/2005 | Purmal et al. | | |
| 2005/0085555 A1 | 4/2005 | Murphy et al. | | |
| 2005/0101676 A1 | 5/2005 | Fahl et al. | | |
| 2012/0014962 A1 | 1/2012 | Mann et al. | | |
| 2012/0142763 A1 * | 6/2012 | Dowdy | ............... | C07H 19/16 |
| | | | | 530/358 |
| 2014/0220573 A1 | 8/2014 | Hrdlicka | | |
| 2014/0329775 A1 * | 11/2014 | Petersen | ............... | C07F 9/65586 |
| | | | | 530/331 |

OTHER PUBLICATIONS

Pons, B. et al., "Online Synthesis of Diblock Cationic Oligonucleotides for Enhanced Hybridization to their Complementary Sequence" ChemBioChem (2006); vol. 7:8, pp. 1173-1176.

Potier, P. et al., "Synthesis of Oligonucleotides Bearing Polyamine Groups for Recognition of DNA Sequences"; Nucleosides & Nucleotides (1999); vol. 18:(6&7); pp. 1467-1468.

Sund, C. et al., "Synthesis of C-branched Spermine Tethered Oligo-DNA and the Thermal Stability of the Duplexes and Triplexes" Tetrahedron (1996); vol. 52:37; pp. 12275-12290.

Zhang, S. et al., "Near-Infrared Fluorescent Oligodeoxyribonucleotide Reporters for Sensing NF-B DNA Interactions In Vitro"; Oligonucleotides (2008); vol. 18:3, pp. 235-244.

Aoki, et al., "Mode of Action of Botulinum Neurotoxins: Current Vaccination Strategies and Molecular Immune Recognition"; Grit Rev Immunol. (2010); vol. 30(2):167-87.

Bovier, P.A., Epaxal(R): a Virosomal Vaccine to Prevent Hepatitis A Infection. Expert Rev Vaccines. Oct. 2008;7(8):1141-50. doi: 10.1586/14760584.7.8.1141.

Griffin, D.E. et al., "Measles Vaccines"; Front Biosci. (2008); vol. 13; pp. 1352-1370.

Thierry-Carstensen, B. et al., Experience with Monocomponent Acellular pertussis combination vaccines for infants, children, adolescents and adults—a review of safety, immunogenicity, efficacy and effectiveness studies and 15 years of field experience. Vaccine. Oct. 25, 2013;31(45):5178-91. doi: 10.1016/j; Vaccine (2013); vol. 31; pp. 5178-5191.

Verma, R. et al., "Whole-cell inactivated leptospirosis vaccine"; Future Prospects. Hum Vaccine Immunother. Apr. 2013;9(4):763-5. doi: 10.4161/hv.23059. Epub Jan. 7, 2013.

\* cited by examiner

HeLa Cells

HeLa Cells

MCF7 Cells

MCF7 Cells

PHOSPHORAMIDITE SYNTHONES FOR THE SYNTHESIS OF SELF-NEUTRALIZING OLIGONUCLEOTIDE COMPOUNDS

RELATED APPLICATIONS

The application is a continuation of U.S. application Ser. No. 15/527,845, filed May 18, 2017, issuing Jul. 28, 2020 as U.S. Pat. No. 10,723,755, which is a 371 of PCT/US2015/061343, filed Nov. 18, 2015, which claims the benefit of priority to U.S. Provisional Application No. 62/081,316, filed Nov. 18, 2014, each of which is incorporated herein by reference in its entirety.

BACKGROUND

Nucleic acids are used as therapeutics, for example, in oligotherapy, antisense therapy, siRNA, and RNAi. However, nucleic acids have low cellular penetration of the nucleic acid.

Antisense based therapies, for example, rely on the hybridization to complementary sequences, to allow for the selective silencing of particular genes. Thus, oligotherapeutics is a very attractive approach for the treatment of cancer, genetic mutations, and even microorganism-mediated diseases.

The main hurdle in achieving the potential therapeutic advantages of these approaches included poor stability of the oligonucleotides and inefficient intracellular penetration of the oligonucleotides. This prompted the development of a large number of synthetic analogs of natural oligonucleotides, such as 2'-position modifications, boranophosphonates, locked nucleic acids, peptide nucleic acids (PNA), morpholino derivatives, alkynyl phosphonates, and terminally modified oligonucleotides. While these modifications improved the biological stability, they did not change the intracellular penetration of oligonucleotides.

To overcome these challenges, different vehicles have been proposed such as virus-based delivery systems, liposome formulations, nanoparticles, and transporter chemical groups. For example, tagging the ends of siRNAs with cholesterol, folate, various peptides, and aptamers can aid in transporting oligonucleotides across cellular barriers or in targeting specific type of cells or organs.

One widely used modification of oligonucleotides is the attachment of amino groups to oligonucleotides via linkers, mostly used as anchor groups for post-synthetic derivatization of synthetic oligonucleotides. The linker is usually attached to the 5'-end of the oligonucleotide upon the completion of automated synthesis. Attachment to the 3'-end on non-standard supports has also been explored. Attachment of linkers to the internucleotide phosphates has been performed as well.

However, despite the development of a large number of chemical modifications of oligonucleotides including different delivery systems, the absence of available oligonucleotides having effective cellular uptake remains an unmet need. Accordingly, there is a need for compositions, compounds and systems for modified oligotherapeutics and to enhance the cellular uptake of oligonucleotides for the treatment of diseases and disorders.

SUMMARY

The present invention relates generally to compositions and compounds having derivatives of synthetic oligonucleotides with one or more charge-neutralizing moieties on their backbone. The compositions and compounds described herein can be used as therapeutic agents (i.e., oligotherapeutics) for the treatment of cancer, autoimmune disorders, genetic diseases, infectious diseases, neurological diseases, inflammatory diseases, metabolic diseases and others.

In some embodiments, the present invention relates to a compound having structure (I):

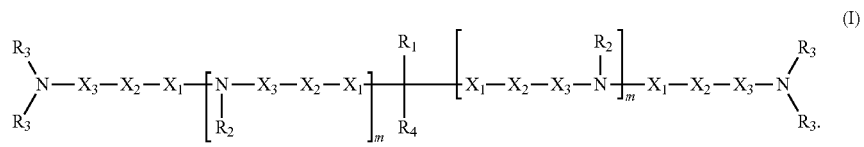

In the compound having structure (I): $R_1$ is a nucleic acid moiety, a spacer group, or a combination thereof. In some embodiments, $R_2$ is, independently for each occurrence, selected from the group consisting of H, $CH_3$, $CH_2CH_3$, an alkyl, a substituted alkyl, a branched chain alkyl, formyl, acetyl, $CF_3$, trifluoroacetyl, allyl, triphenylmethyl, and tert-butyloxycarbonyl. In some embodiments, $R_3$ is, independently for each occurrence, selected from the group consisting of H, F, $CH_3$, $CH_2CH_3$, an alkyl, a substituted alkyl, a branched chain alkyl, formyl, acetyl, $CF_3$, trifluoroacetyl, allyl, triphenylmethyl, tert-butyloxycarbonyl, N-PAC, N-iPrPAC, N-benzoyl, and N-Ac.

In some embodiments, each $R_3$ pair that is bonded to a single nitrogen together form a ringed-structure (e.g., a 5 membered ring, a 6 membered ring, or a 7 membered ring). Examples of nitrogen-containing ringed structures include pyrrolidinyl, piperidinyl, piperazidinyl, and morpholinyl.

In some embodiments, $R_4$ is selected from the group consisting of H, F, $CH_3$, $CH_2CH_3$, $OCH_3$, $OCH_2CH_3$, $OCH(CH_3)_2$, $CH(CH_3)_2$, and $C(CH_3)_3$.

In the compound having structure (I), $X_1$, $X_2$, and $X_3$ are, independently for each occurrence, selected from the group consisting of O, S, $CH_2$, and $CH_2CH_2$. In some embodiments, m is, independently for each occurrence, 0, 1, 2, 3, 4 or 5.

In some embodiments, the compound having structure (I) comprises a pharmaceutically acceptable salt, hydrate, or solvate thereof.

In some embodiments, the nucleic acid moiety has structure (II):

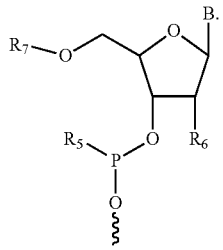

(II)

In some embodiments, $R_5$ in structure (II) is $N(CH(CH_3)_2)_2$. In some embodiments, $R_6$ in structure (II) is selected from the group consisting of protected OH, protected SH, protected $NH_2$, H, $OCH_3$, $OCH_2CH_3$, F, Cl, $N_3$, $OCH_2CH_3$, $OCH_2OCH_2CH_3$, $SCH_3$, and $N(CH_3)_2$.

In some embodiments, $R_7$ in structure (II) is a 5' protecting group and B is a nitrogenous base.

In some embodiments, the compound having structure (I), each $R_3$ is H or $CH_3$, and wherein $X_1$ is $CH_2$, $X_2$ is O, and $X_3$ is $CH_2CH_2$.

In some embodiments, the compound having structure (II), the 5' protecting group is selected from the group consisting of dimethoxytrityl (DMTr), monomethoxytrityl (MMTr), and trityl (Tr).

In some embodiments, the nitrogenous base is a purine or a pyrimidine. For example, a purine can be adenine or guanine; and a pyrimidine can be cytosine, thymine, or uracil. In some embodiments, the nitrogenous base is a modified nitrogenous base. A modified nitrogenous base can include, for example, 5-methylcytosine, pseudouridine, dihydrouridine, 7-methylguanosine, hypoxanthine, xanthine, 7-methylguanine, 5,6-dihydrouracil, 5-methylcytosine, and 5-hydroxymethylcytosine.

In some embodiments, the nitrogenous base comprises a protecting group. Examples of protecting groups include, for example, N-PAC, N-iPrPAC, N-benzoyl, and N-Ac.

In some embodiments, the compound having structure (I) has a spacer group. For example, the spacer group can be $SCH_2$, $OCH_2$, $CH_2OCH_2$, $CH_2SCH_2$, $CH_2$, $CH_2CH_2$ and $CH_2CH_2CH_2$. The spacer group can be covalently bonded between the compound having structure (I) and the nucleic acid moiety.

In some embodiments, the compounds (e.g., having structure (I), (III) and/or (V)) described herein comprise one or more amino groups (e.g., amines) that are positively charged. In some embodiments, at least one of the amino groups is positively charged at a pH of about 6 to about 8. In some embodiments, the at least one of the amino groups is positively charged at a pH of about 6.5 to about 7.5. In some embodiments, the at least one of the amino groups is positively charged at a pH of about 7.0 to about 7.5. In one embodiment, one or more amino groups are positively charged at a pH of about 7.35 to about 7.45. In some embodiments, each amino group in the compounds described herein is positively charged. In one embodiment, each amino group is positively charged at a pH of about 6 to about 8. In one embodiment, each amino group is positively charged at a pH of about 6.5 to about 7.5. In one embodiment, each amino group is positively charged at a pH of about 7.35 to about 7.45.

In some embodiments, at least one terminal nitrogen in the compound having structure (I) comprises an additional $R_3$ group. In some embodiments, at least one of the terminal nitrogen is a quaternary amine. For example, the quaternary amine can be $N(CF_3)_3^+$, $N(CH_3)_3^+$, $N(CH_2CH_3)_3^+$.

In some embodiments, the present invention relates to a compound having structure (III):

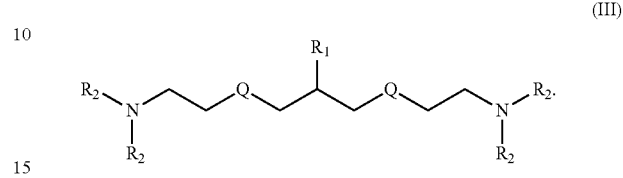

(III)

In the compound having structure (III): $R_1$ is a nucleic acid moiety, a spacer group, or a combination thereof. In some embodiments, $R_2$ is, independently for each occurrence, selected from the group consisting of H, F, $CH_3$, $CH_2CH_3$, an alkyl, a substituted alkyl, a branched chain alkyl, formyl, acetyl, $CF_3$, trifluoroacetyl, allyl, triphenylmethyl, tert-butyloxycarbonyl, N-PAC, N-iPrPAC, N-benzoyl, and N-Ac. In some embodiments, Q is, independently for each occurrence, selected from the group consisting of O, S, $OCH_2$, and $CH_2$.

In some embodiments, the compound having structure (III) comprises a pharmaceutically acceptable salt, hydrate, or solvate thereof.

In some embodiments, the compound having structure (III) has a nucleic acid moiety having structure (II):

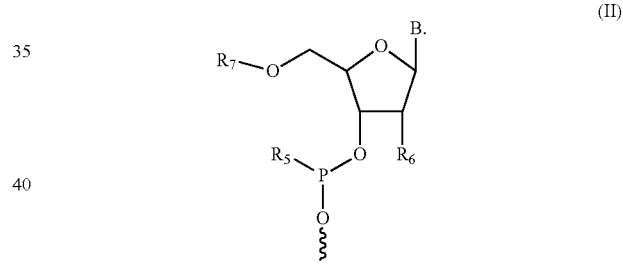

(II)

In some embodiments, $R_5$ is $N(CH(CH_3)_2)_2$. In some embodiments, $R_6$ is selected from the group consisting of protected OH, protected SH, protected $NH_2$, H, $OCH_3$, $OCH_2CH_3$, F, Cl, $N_3$, $OCH_2OCH_3$, $OCH_2OCH_2CH_3$, $SCH_3$, and $N(CH_3)_2$. In some embodiments, $R_7$ is a 5' protecting group; and B is a nitrogenous base.

In some embodiments, the compounds described herein can have one or more nucleotides, thereby forming an oligonucleotide. Some or all of the one or more nucleotides can comprise, for example, a naturally occurring nucleotide and/or a non-naturally occurring nucleotide (e.g., a modified nucleotide and/or a synthetic nucleotide). Each modified nucleotide can have a neutralizing moiety and can include nucleoside phosphoramidites and derivatives thereof.

In some embodiments, the present invention relates to an oligonucleotide. The oligonucleotide can comprise an oligonucleotide sugar-phosphate backbone, a plurality of nitrogenous bases, each nitrogenous base covalently bonded to a sugar unit of the sugar-phosphate backbone, and at least one neutralizing moiety covalently bonded to a phosphorus of the sugar-phosphate backbone. As used herein "neutralizing moiety" can include compounds having structure (V):

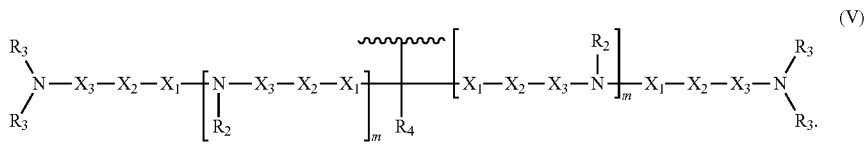

(V)

In the compound having structure (V): $R_2$ and $R_3$ are, independently for each occurrence, selected from the group consisting of H, $CH_3$, $CH_2CH_3$, an alkyl, a substituted alkyl, and a branched chain alkyl. In some embodiments, $R_4$ is selected from the group consisting of H, F, $CH_3$, $CH_2CH_3$, $OCH_3$, $OCH_2CH_3$, $OCH(CH_3)_2$, $CH(CH_3)_2$, and $C(CH_3)_3$.

In the compound having structure (V), $X_1$, $X_2$, and $X_3$ are, independently for each occurrence, selected from the group consisting of O, S, $CH_2$, and $CH_2CH_2$. In some embodiments, m is, independently for each occurrence, 0, 1, 2, 3, 4 or 5.

In some embodiments, the oligonucleotides described herein can be a single stranded oligonucleotide or a double stranded oligonucleotide. In some embodiments, the oligonucleotide can be an oligodeoxyribonucleotide, an oligoribonucleotide, or a small interfering oligoribonucleotide. In some embodiments, the oligonucleotide comprises about 5 to about 500 nitrogenous bases. In some embodiments, the oligonucleotide comprises about 1 to about 500 neutralizing moieties.

Another embodiment of the present invention includes using the compounds, neutralizing moieties and/or oligonucleotides described herein to treat a disease or a disorder. A method of treating a disease or a disorder in a person in need thereof can comprise administering an oligonucleotide to the person. The oligonucleotide comprises at least one neutralizing moiety having structure (V) (shown herein) and the oligonucleotide is delivered to a cell and modulates a cellular response.

In some embodiments, the disease or disorder is a cancer, an autoimmune disorder, a genetic disease, an infectious disease, a neurological disease, an inflammatory disease, a metabolic disease or a combination thereof.

In some embodiments, the compounds and compositions described herein can be used as a oligotherapy. For example, an oligotherapy can include an antisense therapy, an siRNA therapy, and/or a RNAi therapy.

In some embodiments, method of modulating a cellular response can be in any cell. For example, the cell be an eukaryotic cell and/or a prokaryotic cell. In some embodiments, the methods described herein allow for modulation of other non-cellular based agents, such as viruses and prions.

In some embodiments, the method comprises administering a compound (e.g., having structures (I), (III), and/or (V)) comprising a pharmaceutically acceptable salt, hydrate, or solvate thereof.

Further understanding of the invention can be obtained by reference to the following detailed description in conjunction with the associated drawings, which are described briefly below.

BRIEF DESCRIPTION OF DRAWINGS

FIG. 5B), SEQ ID NO:5 (ZT5; FIG. 5C), and SEQ ID NO:6 (ZT6; FIG. 5D) are shown at 40×.

FIG. 6B), SEQ ID NO:5 (ZT5; FIG. 6C), and SEQ ID NO:6 (ZT6; FIG. 6D) are shown at 40×.

FIG. 9B) and SEQ ID NO:17 (ZT17; FIG. 9C) in A172 cells after 2.5 hours of incubation.

(FIG. 10C) of incubation.

FIG. 11A shows part of the structure of SEQ ID NO:23 (ZT23; 13mer), described herein. Two neutralizing moieties, defined by structure (V), neutralize negative charges on the sugar-phosphate backbone. Each neutralizing moiety has 2 terminal quaternary amines $(NHCH3)_2+)$.

FIGS. 11B-11G illustrates other embodiments of oligonucleotides having structures (III) and (II). FIGS. 11H-11I illustrates other embodiments of oligonucleotides having structures (I) and (II).

DETAILED DESCRIPTION

The present invention relates generally to compositions and compounds having derivatives of synthetic oligonucleotides with one or more charge-neutralizing moieties, and methods of making and using the same. The compositions and compounds described herein can be used as therapeutic agents (i.e., oligotherapeutics) for the treatment of cancer, autoimmune disorders, genetic diseases, infectious diseases, neurological diseases, inflammatory diseases, metabolic diseases and others.

The compounds can have one or more nucleotides, thereby forming oligonucleotides.

Some or all of the one or more nucleotides can comprise a naturally occurring nucleotide and/or a non-naturally occurring nucleotide (e.g., a modified nucleotide and/or a synthetic nucleotide).

Each modified nucleotide can have a neutralizing moiety and can include nucleoside phosphoramidites and derivatives thereof. These compounds can have one or more amino groups that are or can be positively charged. As described herein, the compounds have chemical structures that promote hybridization (e.g., ion pair) with one or more phosphate groups in a nucleic acid molecule The compositions and compounds can neutralize (e.g., self-neutralize) one or more negative charges on a nucleic acid molecule (e.g, DNA, RNA). The compounds provided herein can also enhance cell membrane penetration and/or cellular uptake. For example, the compounds described herein can neutralize all or some of the charge found on oligonucleotides (e.g., nucleic acid molecules). By neutralizing all or some of the charge, the nucleic acid molecule can enter a cell (e.g., a eukaryotic cell, a prokaryotic cell). The compounds can also penetrate through cell membranes, cell walls, and/or capsids of organisms and pathogens.

The compositions and compounds of the present invention can allow for a low number of charges and/or presence of some degree of hydrophobicity across a backbone. Also, the compounds described herein can have: the ability to maintain natural hybridization properties with a target nucleic acid sequence (e.g., gene), sufficient water solubility, stability in the presence of a nuclease, low toxicity at a therapeutic concentration, and/or an ability to silence a target gene by activation of an cellular system (e.g., enzyme) or to block a target gene by selective hybridization.

The known modifications of oligonucleotides described above have satisfied some but not all of these criteria. Embodiments of the present invention address and solve the problem with cellular uptake of oligonucleotides as described in the main body of this invention.

The compounds and methods provided herein can also be used for the treatment of diseases and disorders, such as cancer, autoimmune disorders, genetic diseases, infectious diseases, neurological diseases, inflammatory diseases, metabolic diseases and others.

Figure 1A:
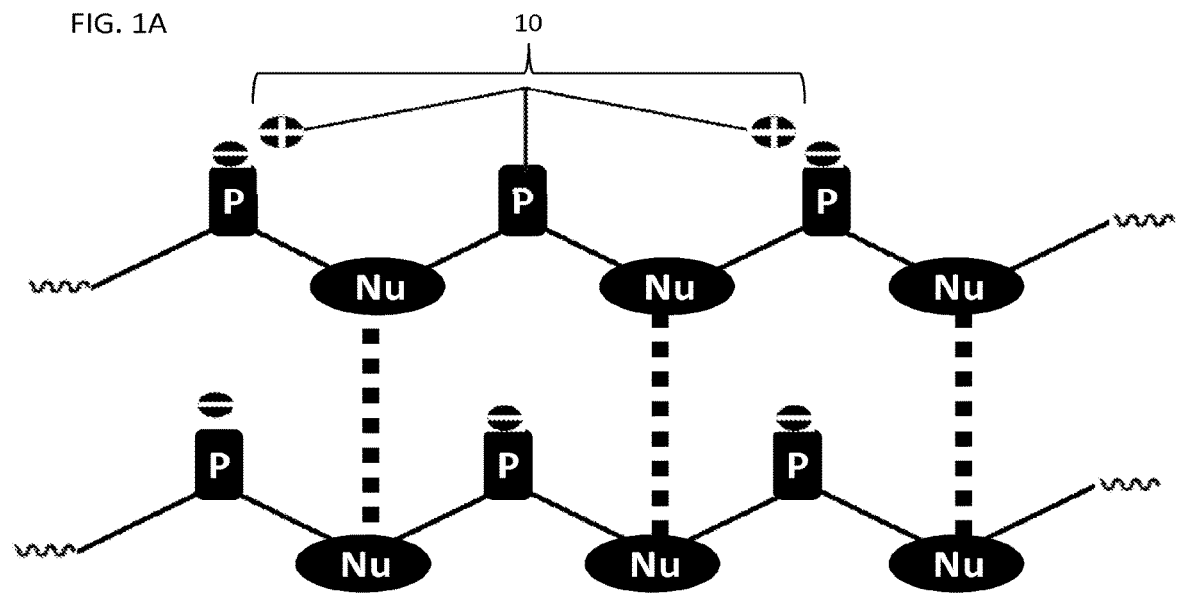
FIGS. 1A-1B illustrate hybridized oligonucleotides comprising neutralizing moieties for the neutralization of negative charges in according to the present invention.
Figure 1B:
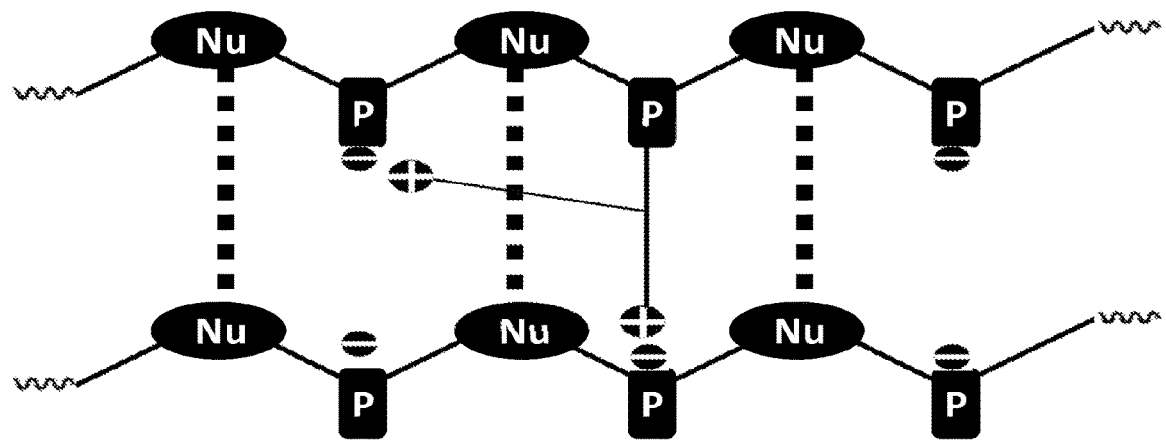

A schematic of the compositions and compounds described herein are illustrated in FIGS. 1A-1B and 2A-2E. FIGS. 1A-1B illustrate the neutralization of negative charges in a hybridized oligonucleotide according to the present invention. The length of neutralizing moiety 10 can be optimized so that terminal positive charges can reach and neutralize neighboring (adjacent) negative charges, e.g., from phosphate groups, on the same strand as illustrated in FIG. 1A. The positive charges on neutralizing moiety 10 can also reach and neutralize negative charges in a hybridized (opposite) strand as illustrated FIG. 1B. Referring to FIGS. 1A-1B, "Nu" refers to nucleoside or nucleoside analog, "P" refers to phosphate, "+" refers to a positive charge, and"−" refers to a negative charge. The dotted lines in FIGS. 1A-1B illustrate hydrogen bonding between nitrogenous bases.

Figures 2A, 2B, 2C, 2D, 2E:
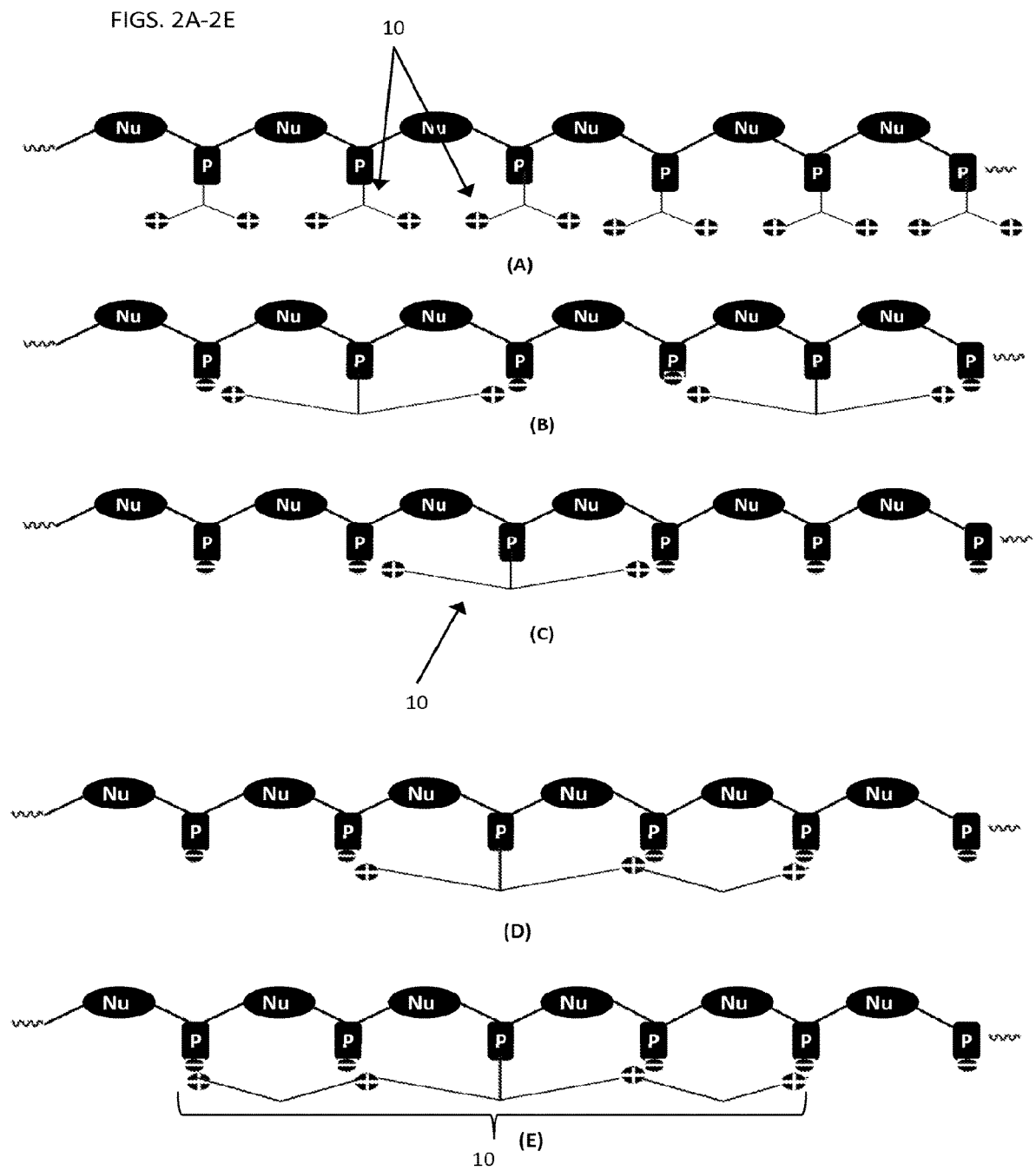
FIGS. 2A-2E illustrate other oligonucleotides of the present invention neutralizing moieties reducing the overall charge.

FIGS. 2A-2E illustrate other embodiments of the compounds of the present invention having neutralizing moieties 10, reducing the overall charge of an oligonucleotide. FIG. 2A illustrates an oligonucleotide with a neutralizing moiety 10 on each phosphate illustrated. Each neutralizing moiety 10 illustrated in FIG. 2A comprises two branched chemical groups. Each branched chemical group has a single positive charge at a terminal end. As illustrated in FIG. 2A, each neutralizing moiety 10 contributes two positive charges to the overall structure of the oligonucleotide. FIG. 2B illustrates an oligonucleotide having two neutralizing moieties, each neutralizing moiety having two branched chemical groups. At the terminal end of each branched chemical group is a positive charge. As described herein, the positive charge can neutralize a neighboring phosphate charge. FIG. 2C illustrates an oligonucleotide similar to FIG. 2B, having one neutralizing moiety 10. FIG. 2D illustrates an oligonucleotide having a neutralizing moiety having two branched chemical groups. One branched chemical group has a single positive charge and the second branched group has two positive charges. FIG. 2E illustrates an oligonucleotide having a neutralizing moiety 10 having two branched chemical groups. In FIG. 2E, each branched chemical group has two positive charges—a terminal positive charge and an internal positive charge.

In some embodiments, an oligonucleotide can have a neutralizing moiety on some or all of the phosphates. For example, an oligonucleotide can have 1 or more, 2 or more, 3 or more, 4 or more, 5 or more, 10 or more, 20 or more, 50 or more, or 100 or more neutralizing moieties.

In some embodiments, a neutralizing moiety can contain at least a single positive charge.

For example, a neutralizing moiety (e.g., see FIGS. 1A-2E) can have 2, 3, 4, 5, 6, 7, 8, 9, 10, or more positive charges.

In one embodiment, the invention relates to a composition comprising a compound having structure (I):

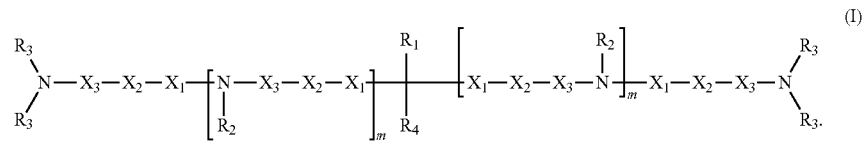

(I)

In some embodiments of the compound having structure (I), $R_1$ is a nucleic acid moiety, a spacer group, or a combination thereof. As used herein, a "nucleic acid moiety" refers to any compound having a base (e.g. natural or non-natural nitrogenous base), sugar unit, and a 3 or 5 valent phosphorus atom. These include naturally occurring nucleic acid moieties (e.g., nucleotides) and non-naturally occurring nucleic acid moieties (e.g., synthetic or derivatives of naturally occurring nucleic acid moieties). For example, a nucleic acid moiety can have a phosphate (nucleotide), a phosphoroamidite (e.g., nucleoside 3'-phosphoramidite), a H-phosphonate (e.g., nucleoside 3'-H-phosphonate), or derivatives thereof In some embodiments, the compound having structure (I) and/or (III) has a spacer group.

For example, the spacer group can be $SCH_2$, $OCH_2$, $CH_2OCH_2$, $CH_2SCH_2$, $CH_2$, $CH_2CH_2$ or $CH_2CH_2CH_2$. The spacer group can be covalently bonded between the compound having structure (I) or (III) and the nucleic acid moiety.

In some embodiments of the compound having structure (I), $R_2$ is, independently for each occurrence, selected from the group consisting of H, $CH_3$, $CH_2CH_3$, an alkyl, a substituted alkyl, a branched chain alkyl, formyl, acetyl, $CF_3$, trifluoroacetyl, allyl, triphenylmethyl, and tert-butyloxycarbonyl.

In some embodiments of the compound having structure (I), $R_3$ is, independently for each occurrence, selected from the group consisting of H, F, $CH_3$, $CH_2CH_3$, an alkyl, a substituted alkyl, a branched chain alkyl, formyl, acetyl, $CF_3$, trifluoroacetyl, allyl, triphenylmethyl, tert-butyloxycarbonyl, N-PAC, N-iPrPAC, N-benzoyl, and N-Ac.

In other embodiments of the compound having structure (I), each pair of terminal $R_3$ groups form a ringed structure with the nitrogen. For example, the ringed structure can comprise a 5 membered ring, 6 membered ring, or a 7 membered ring. In each instance, the ringed structure contains nitrogen. For example, a nitrogen containing ring can be a pyrolidine, piperidine, piperazine, or morpholine group (i.e., pyrrolidinyl, piperidinyl, piperazidinyl, and morpholinyl).

In some embodiments of the compound having structure (I), $R_4$ is selected from the group consisting of H, F, $CH_3$, $CH_2CH_3$, $OCH_3$, $OCH_2CH_3$, $OCH(CH_3)_2$, $CH(CH_3)_2$, and $C(CH_3)_3$.

In the compound having structure (I), $X_1$, $X_2$, and $X_3$ are, independently for each occurrence, selected from the group consisting of O, S, $CH_2$, and $CH_2CH_2$. In some embodiments, m is, independently for each occurrence, 0, 1, 2, 3, 4 or 5.

For example, the compound having structure (I), each $R_3$ is H or $CH_3$, and $X_1$ is $CH_2$, $X_2$ is O, and $X_3$ is $CH_2CH_2$.

In some embodiments, the compound having structure (I) comprises a pharmaceutically acceptable salt, hydrate, or solvate thereof.

In another embodiment, the present invention relates to a compound having structure (III):

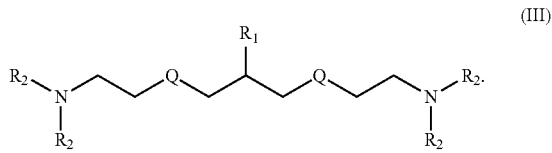

(III)

In some embodiments of the compound having structure (III), $R_1$ is a nucleic acid moiety, a spacer group, or a combination thereof. In some embodiments, $R_2$ is, independently for each occurrence, selected from the group consisting of H, F, $CH_3$, $CH_2CH_3$, an alkyl, a substituted alkyl, a branched chain alkyl, formyl, acetyl, $CF_3$, trifluoroacetyl, allyl, triphenylmethyl, tert-butyloxycarbonyl, N-PAC, N-iPrPAC, N-benzoyl, and N-Ac. In some embodiments, Q is, independently for each occurrence, selected from the group consisting of O, S, $OCH_2$, and $CH_2$.

In some embodiments, the compound having structure (III) comprises a pharmaceutically acceptable salt, hydrate, or solvate thereof.

In some embodiments, the compounds (e.g., having structures (I), (III), and/or (V)) described herein comprise one or more amino groups. The one or more amino groups can be a primary amine, a secondary amine, a tertiary amine, a quaternary amine, a cyclic amine, or a combination thereof. As used herein "amine" and "amino" are used interchangeably to refer to an organic compound containing a basic nitrogen atom.

In some embodiments, the compounds (e.g., having structures (I), (III), and/or (V)) described herein, have 1 or more, 2 or more, 3 or more, 4 or more, 5 or more, 6 or more, 7 or more, 8 or more, 9 or more, or 10 or more amino groups. In one embodiment, the compound has 1 amino group. In one embodiment, the compound has 2 amino groups. In one embodiment, the compound has 3 amino groups. In one embodiment, the compound has 4 amino groups. In one embodiment, the compound has 5 amino groups. In one embodiment, the compound has 6 amino groups.

In some embodiments, some or all of the amino groups (e.g., in a neutralizing moiety) can be positively charged. For example, 1, 2, 3, 4, 5, 6, or more of the amino groups (amines) in a neutralizing moiety are positively charged. The positive charge can occur in a variety of ways and conditions. For example, the amine can be a quaternary amine, so that the nitrogen is always charged. In other embodiments, the amine is a protonated primary, secondary, tertiary or cyclic amine. For example, the amine can be protonated under certain conditions, such as pH. In some embodiments, at least one amino group is positively charged at a pH of about 6 to about 8 in the compound having structure (I), (III), and/or (V). In some embodiments, at least one amino group is positively charged at a pH of about 6.5 to about 7.5. In some embodiments, at least one of the amino group is positively charged at a pH of about 7.0 to about 7.5. In one embodiment, one or more amino groups are positively charged at a pH of about 7.35 to about 7.45. In some embodiments, each (i.e., all) amino group in the compounds described herein is positively charged.

In some embodiments, each terminal nitrogen in the compound, e.g., having structure (I), comprises an additional $R_3$ group. In some embodiments, at least one of the terminal amino groups is a quaternary amine. For example, the quaternary amine can be $N(CF_3)_3^+$, $N(CH_3)_3^+$, $N(CH_2CH_3)_3^+$.

In some embodiments, at least one positive charge (e.g., on an amine) in the compounds described herein, e.g., having structure (I), (III), and/or (V), can form an ion pair. The ion pair can be intramolecular, e.g., it binds to another part of the same molecule (e.g., nucleic acid molecule). For example, the structures of the compounds described herein can allow for a terminal amino group (e.g., that is positively charged) to bind to a phosphate group (e.g., that is negatively charged) that is part of the same nucleic acid molecule. The structures of the compounds described herein can also allow for a terminal amino group (e.g., that is positively charged) to bind to a phosphate group (e.g., that is negatively charged) that is part of a different nucleic acid molecule. The phosphate group can be an adjacent phosphate group (i.e., directly next to). The adjacent phosphate group can be at a 5' end or a 3' end.

The compounds described herein can self-neutralize charges found within the same compound and/or in a different compound (e.g., a hybridized compound). For example, the positive charge(s) can neutralize charge found in a sugar-phosphate backbone of an oligonucleotide compound.

In some embodiments of the compound having structure (I) and/or (III), the nucleic acid moiety has structure (II):

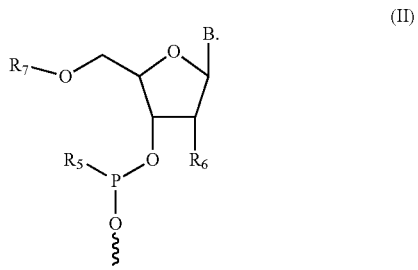

(II)

In some embodiments, $R_5$ in structure (II) is $N(CH(CH_3)_2)_2$.

In some embodiments, $R_6$ in structure (II) is selected from the group consisting of OH, SH, $NH_2$, H, $OCH_3$, $OCH_2CH_3$, F, Cl, $N_3$, $OCH_2OCH_3$, $OCH_2OCH_2CH_3$, $SCH_3$, and $N(CH_3)_2$. It will be readily apparent to one of ordinary skill in the art, that OH, SH and $NH_2$ groups can be protected. For example, OH can be protected with acetyl, TOM and/or TBDMS. For example, SH can be protected with TOM. For example, $NH_2$ can be protected with acetyl and/or trifluoroacetyl.

In some embodiments, $R_7$ in structure (II) is a 5' protecting group. For example, the 5' protecting group is selected from the group consisting of dimethoxytrityl (DMTr), monomethoxytrityl (MMTr), and trityl (Tr).

In some embodiments, B in structure (II) is a nitrogenous base. For example, the nitrogenous base can be a purine or a pyrimidine. For example, a purine can be adenine or guanine; and a pyrimidine can be cytosine, thymine, or uracil. In some embodiments, the nitrogenous base is a modified nitrogenous base.

Examples of a modified nitrogenous base can include 5-methylcytosine, pseudouridine, dihydrouridine, 7-methylguanosine, hypoxanthine, xanthine, 7-methylguanine, 5,6-dihydrouracil, 5-methylcytosine, and 5-hydroxymethylcytosine.

Examples of modified nucleosides include 5-methylcytidine (5mC), pseudouridine (Ψ), 5-methyluridine, 2' O-methyluridine, 2-thiouridine, N-6 methyladenosine, hypoxanthine, dihydrouridine (D), inosine (I), and 7-methylguanosine (m7G). It should be noted that any number of bases in the oligonucleotides described herein can be substituted with one or more modified nucleosides (or nitrogenous base). Tt should further be understood that combinations of different modifications may be used.

In some embodiments, the nitrogenous base comprises a protecting group. Examples of protecting groups include, for example, N-PAC, N-iPrPAC, N-benzoyl, and N-Ac.

The compounds of the present invention can be used as monomers (e.g., a modified nucleic acid monomer) in the synthesis of oligomers (e.g., oligonucleotides). In some embodiments, the present invention relates to an oligonucleotide. The oligonucleotide can comprise an oligonucleotide sugar-phosphate backbone, a plurality of nitrogenous bases, each nitrogenous base covalently bonded to a sugar unit of the sugar-phosphate backbone, and at least one neutralizing moiety covalently bonded to a phosphorus of the sugar-phosphate backbone.

In some embodiments of the compound having structure (I), the nucleic acid moiety comprises a sugar-phosphate backbone. As used herein, a "sugar-phosphate backbone" refers to any backbone structure of an oligonucleotide (e.g., a nucleic acid sequence). For example, the "phosphate" can refer to phosphate ($PO_4^-$), $PSO_3^-$, $PS_2O_2^-$, $PO_4D$, or $PSO_3D$. "D" can refer to CHI or a neutralizing moiety having structure (V). The "sugar" can refer to any sugar, such as a pentose (e.g., ribose, deoxyribose) or modified pentose.

As used herein "neutralizing moiety" can include compounds having structure (V):

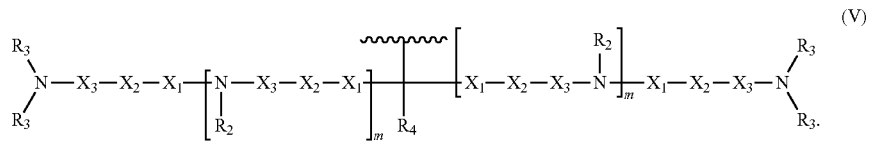

(V)

In some embodiments of the compound having structure (V), $R_2$ and $R_3$ are, independently for each occurrence, selected from the group consisting of H, $CH_3$, $CH_2CH_3$, an alkyl, a substituted alkyl, and a branched chain alkyl. In some embodiments, $R_4$ is selected from the group consisting of H, F, $CH_3$, $CH_2CH_3$, $OCH_3$, $OCH_2CH_3$, $OCH(CH_3)_2$, $CH(CH_3)_2$, and $C(CH_3)_3$.

In some embodiments of the compound having structure (V), $X_1$, $X_2$, and $X_3$ are, independently for each occurrence, selected from the group consisting of O, S, $CH_2$, and $CH_2CH_2$. In some embodiments, m is, independently for each occurrence, 0, 1, 2, 3, 4 or 5.

Figure 11A:
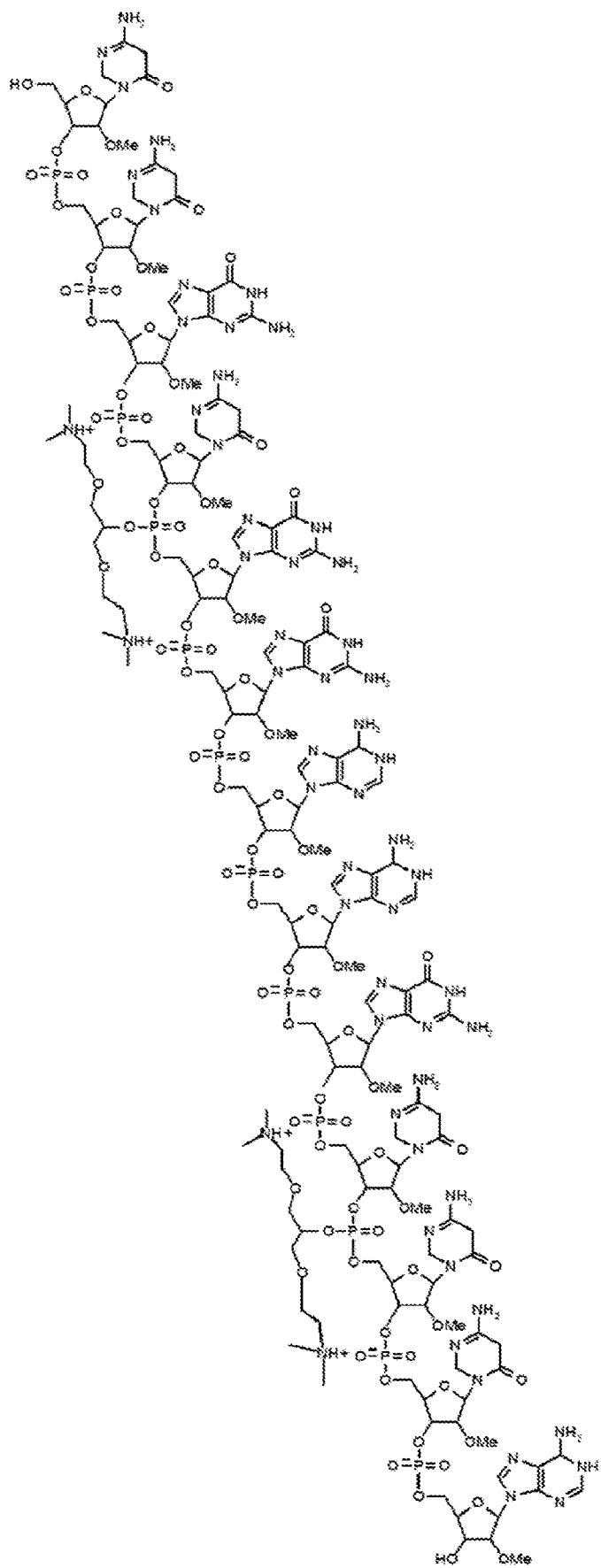
FIGS. 11A-11I illustrate various embodiments of the compounds (e.g., oligonucleotides) according to the present invention.
Figure 11B:
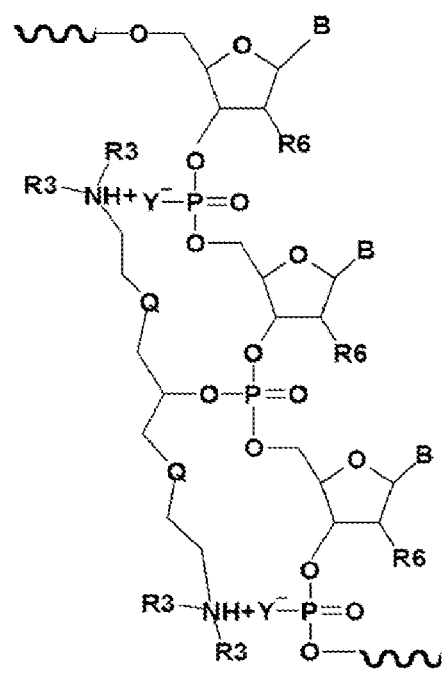
Figure 11C:
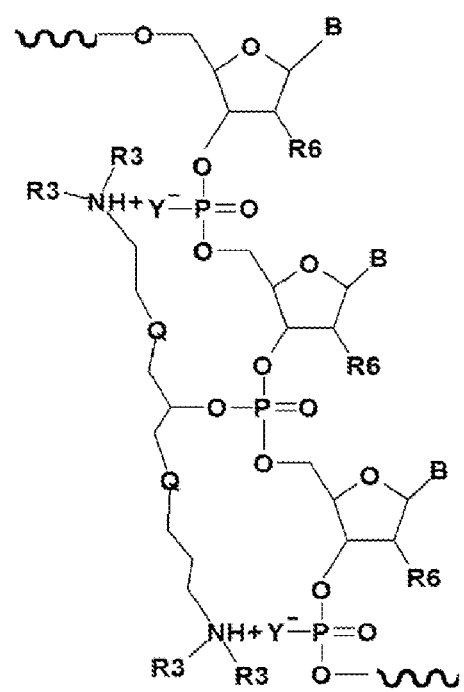
Figure 11D:
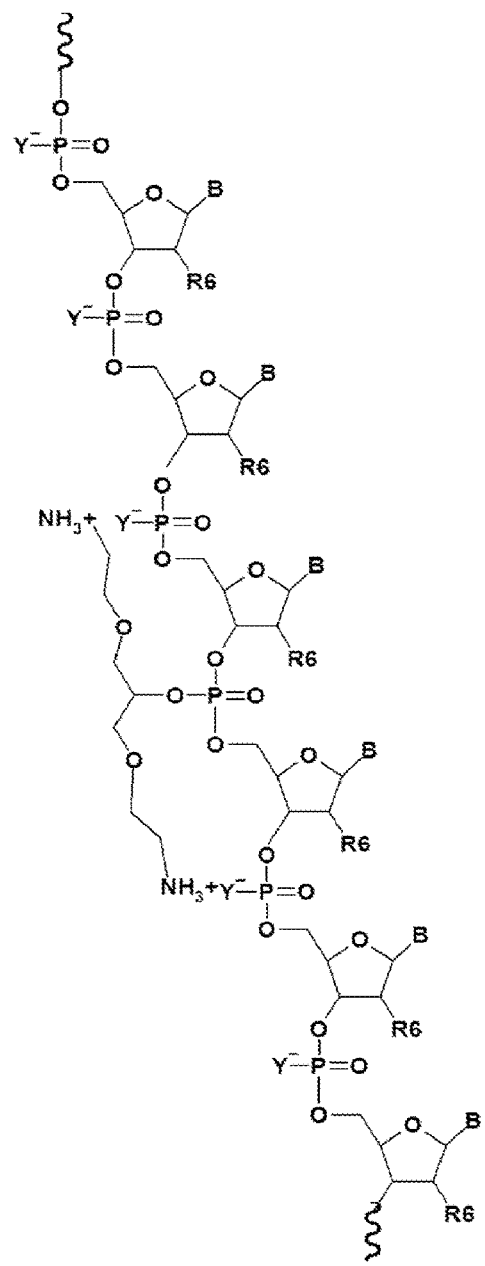
Figure 11E:
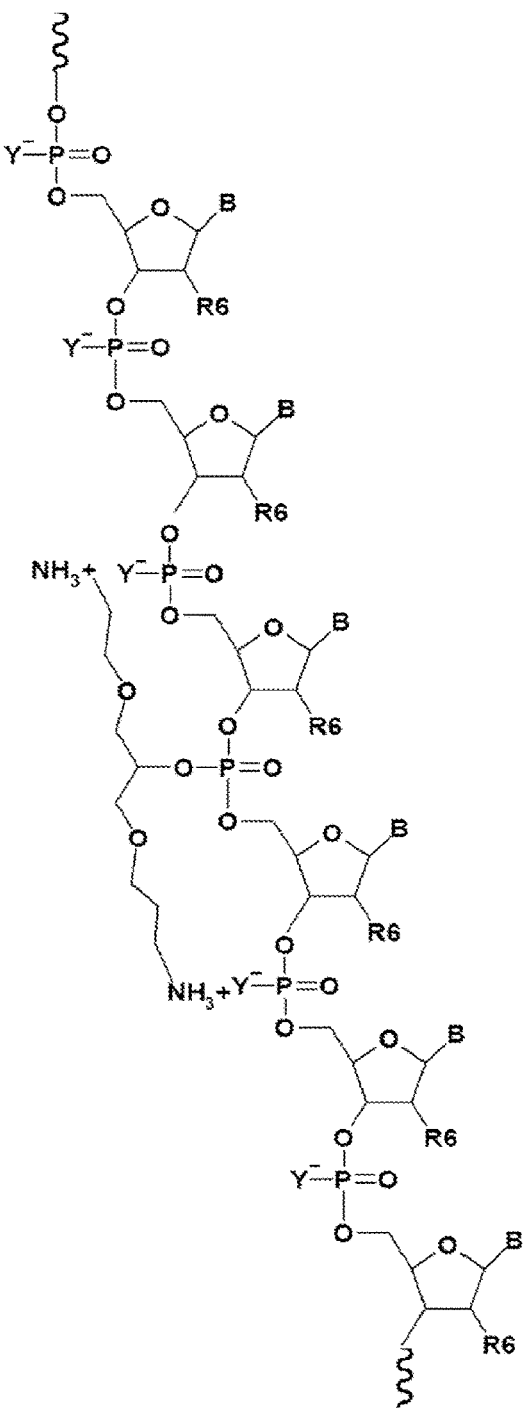
Figure 11F:
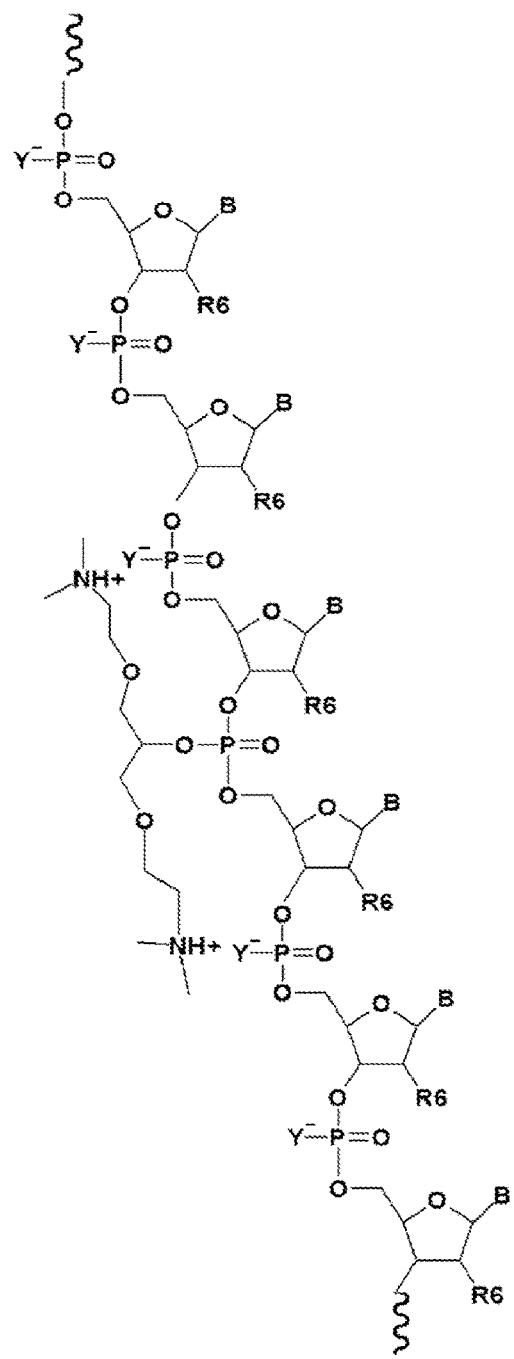
Figure 11G:
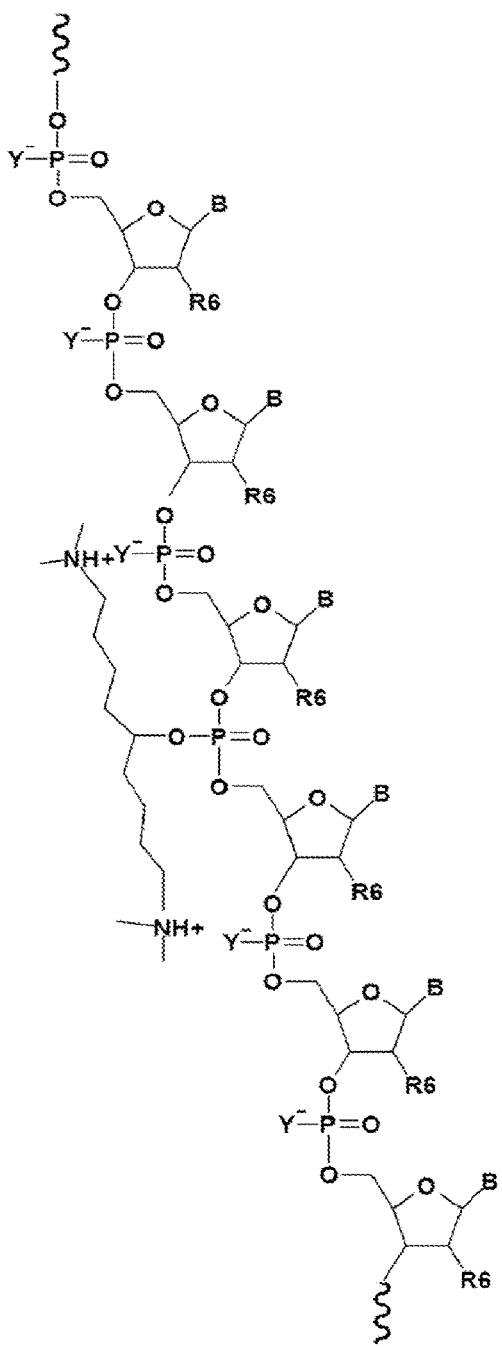
Figure 11H:
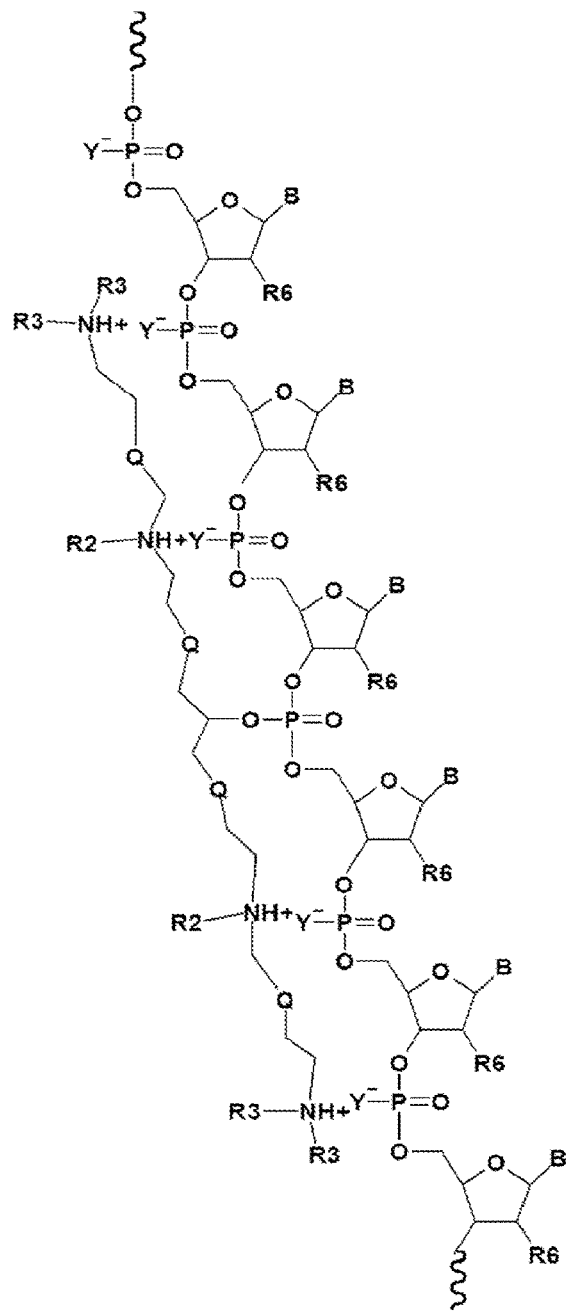
Figure 11I:
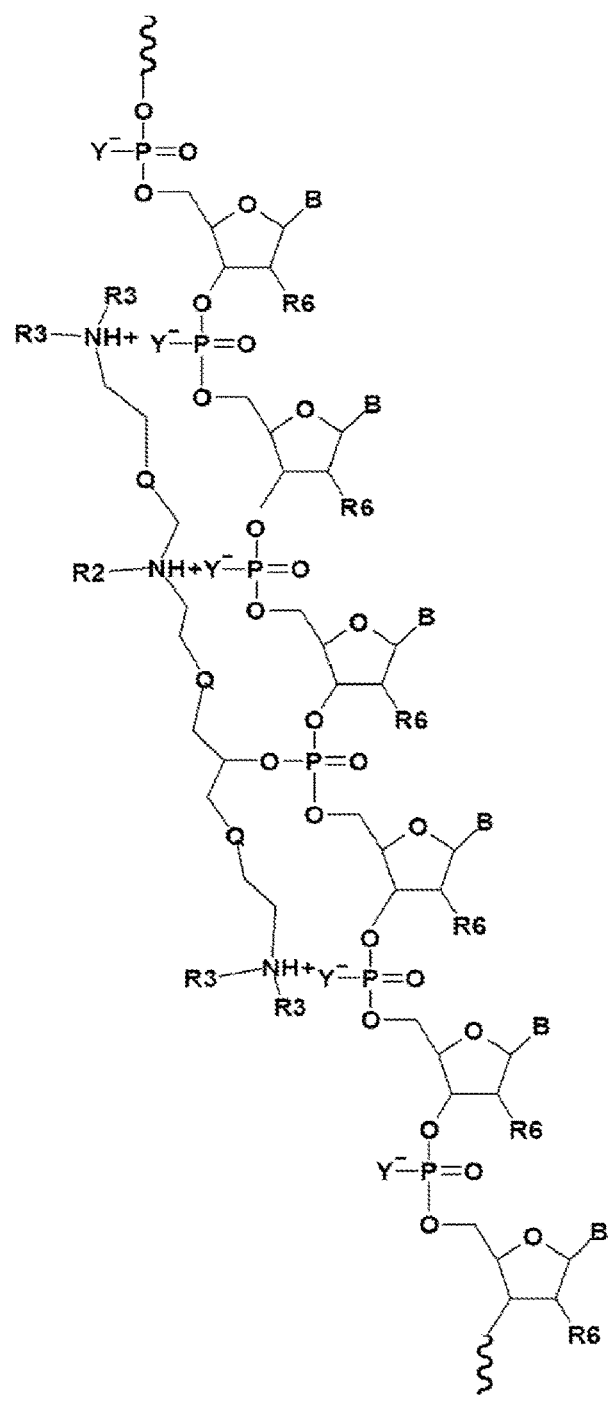

FIGS. 11A-11I illustrate various embodiments of the compounds (e.g., oligonucleotides) according to the present invention. FIG. 11A shows part of the structure of SEQ ID NO:23 (ZT23; 13mer), described herein. Two neutralizing moieties, defined by structure (V), neutralize negative charges on the sugar-phosphate backbone. Each neutralizing moiety has 2 terminal quaternary amines ($NHCH_3)_2^+$). FIGS. 11B-11G illustrates other embodiments of oligonucleotides having structures (III) and (II). FIGS. 11H-11I illustrates other embodiments of oligonucleotides having structures (I) and (II).

In some embodiments, the oligonucleotides described herein can be a single stranded (ss) oligonucleotide or a double stranded (ds) oligonucleotide. In some embodiments, the oligonucleotide can be an oligodeoxyribonucleotide, an oligoribonucleotide, a small interfering oligoribonucleotide, or modified oligonucleotides thereof. The oligonucleotide can be a linear oligonucleotide. The oligonucleotide can be a circular oligonucleotides.

In some embodiments, the oligonucleotide sequence can vary in length. In some embodiments, the oligonucleotide can be about 5 bases to about 500 (nitrogenous) bases.

In some embodiments, the oligonucleotide can be about 10 to about 300 bases; about 15 to about 150 bases; about 20 to about 200 bases; about 30 to about 100 bases; about 40 to about 75 bases; or about 50 to about 70 bases in length. In some embodiments, the oligonucleotide has 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 40 or more, 50 or more, 100 or more, 200 or more, 300 or more, or 400 or more, up to about 500 (contiguous) nitrogenous bases.

In accordance with the teachings of the present invention, the compounds (e.g., oligonucleotides) can target (e.g., bind to, hybridize to) a specific nucleic acid sequence in a cell.

The portion of the oligonucleotide sequence that is complementary to a target nucleic acid sequence can also vary in size. In particular embodiments, the portion of each target nucleic acid sequence to which the oligonucleotide is complementary can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, 100 or more nucleotides (contiguous nucleotides) in length. In some embodiments, each oligonucleotide sequence can be at least about 70%, 75%, 80%, 85%, 90%, 95%, 100%, etc. identical or similar to the portion of each target nucleic acid sequence. In some embodiments, each oligonucleotide sequence is completely or partially identical or similar to each target nucleic acid sequence. For example, each oligonucleotide sequence can differ from perfect complementarity to the portion of the target sequence by about 1, 2, 3, 4, 5, 6, 7, 8, 9, 10, 11, 12, 13, 14, 15, 16, 17, 18, 19, 20, etc. nucleotides. In some embodiments, the oligonucleotide sequences is perfectly complementary (100%) across at least about 5 to about 50 (e.g., about 20) nucleotides of the target nucleic acid.

In some embodiments, the oligonucleotide comprises about 1 to about 500 neutralizing moieties. For example the oligonucleotide has 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 50 or more, 100 or more, 200 or more, or 400 or more neutralizing moieties.

In some embodiments, the oligonucleotides described herein can be covalently bonded to (e.g., conjugated with) another chemical moiety, forming a conjugated complex. For example, a chemical moiety that can be bonded with the oligonucleotides described herein can be any chemical moiety, such as, a non-nucleotide chemical moiety, a linear chemical moiety, a branched chemical moiety, a cyclic (homo and hetero) chemical moiety, an aromatic chemical moiety, a hydrophobic chemical moiety, a hydrophilic chemical moiety, one or more amino acids, a peptide, a protein, a steroid, a cholesterol, a triglyceride, a fluorochrome, an antibiotic, a vitamin, a sugar, an antibody or fragment thereof, and/or combinations thereof. It will be readily apparent to one of ordinary skill in the art to enhance or modulate the function of the compounds described herein. That is, a purpose of the oligonucleotide can provide targeting to specific target structures (e.g., nucleic acid sequences). A conjugated complex can, for example, increase affinity to those target structures. A conjugated complex can facilitate transport across biological structures (e.g., cell membranes, cell walls, etc.). A conjugated complex can modulate biophysical or biochemical properties such as, for example, bioavailability, hydrophobicity, solubility, and/or stability.

The composition, compounds, and oligonucleotides of the present invention can be synthesized that is apparent to one of ordinary skill in the art. For example, unique nucleic acid sequences (e.g, oligonucleotides) can be synthesized using the compounds and neutralizing moieties according to the teachings of the present invention. Nucleic acid sequences can target (e.g., hybridize, bind, etc.) a complementary sequence in a cell. The complementary sequence, for example, can be any nucleic acid sequence, such as a DNA sequence or RNA (e.g., mRNA, tRNA, rRNA, etc.) sequence. Complementary sequences can also comprise a genomic sequence, a gene.

In some embodiments a gene encodes a polypeptide. In some embodiments a gene may not encode a polypeptide. A gene may, for example, comprise a template for transcription of a functional RNA, i.e., an RNA that has at least one function other than providing a messenger RNA (mRNA) to be translated into protein. Examples, include, e.g., long non-coding RNA (e.g., greater than 200 bases in length, e.g., 200-5,000 bases), small RNA (e.g., small nuclear RNA), transfer RNA, ribosomal RNA, microRNA precursor, Piwi-interacting RNAs (piRNAs), small nucleolar RNAs (snoR-NAs). In some embodiments a small RNA is 25 bases or less, 50 bases or less, 100 bases or less, 200 bases or less in length. In some embodiments a genomic sequence may be suspected of potentially comprising a template for transcription of a functional RNA. A genetic modification may be made in the sequence to determine whether such genetic modification alters the phenotype of a cell or animal or affects production of an RNA or protein or alters susceptibility to a disease.

In some embodiments it is of interest to genetically modify a known or suspected regulatory region, e.g., a known or suspected enhancer region or a known or suspected promoter region. The effect on expression of one or more genes in (e.g., within up to about 1, 2, 5, 10, 20, 50, 100, 500 kB or within about 1, 2, 5, or 10 MB from the gene) may be assessed. Binding to the regulatory region can modulate the phenotype of a cell or animal or affects production of an RNA or protein or alters susceptibility to a disease.

The compositions and compounds of the present invention can be used to treat a disease and/or a disorder. A method of treating a disease or a disorder in a person in need thereof can comprise administering an oligonucleotide to the person, wherein the oligonucleotide comprises at least one neutralizing moiety having structure (V) (shown herein) and wherein the oligonucleotide is delivered to a cell and modulates a cellular response.

In some embodiments, method of modulating a cellular response can be in any cell. For example, the cell be an eukaryotic cell and/or a prokaryotic cell. Eukaryotic cells include, for example, animal cells (e.g., pigs, mice, rats, sheep, cows, dogs, guinea pigs, non-human primates, humans), plant cells and fungal cells. Prokaryotic cells include, for example, bacterial cells, archaeal cells. In some embodiments, the methods described herein allow for modulation of other non-cellular based agents, such as viruses and prions.

In some embodiments, the oligonucleotides can be used as an oligotherapy or any therapeutic that uses one or more nucleic acids. Examples of oligotherapies can include antisense therapy, siRNA therapy, RNAi therapy. Oligotherapy can be used, for example for genetic disorders or infections. The oligonucleotides described herein can be synthesized so that it can bind to, hybridize, or otherwise be complementary to a genetic sequence of a particular gene. In some embodiments, the oligonucleotide binds to and modulates (e.g., inactivates) a mRNA produced by that gene. Alternatively, in other embodiments, the oligonucleotide can target a splicing site on pre-mRNA or another site and modify an exon content of an mRNA.

The oligonucleotides described herein can be used in antisense therapies for diseases such as cancers (including lung cancer, colorectal carcinoma, pancreatic carcinoma, malignant glioma and malignant melanoma), diabetes, Amyotrophic lateral sclerosis (ALS), Duchenne muscular dystrophy and diseases such as asthma, arthritis and pouchitis with an inflammatory component.

In some embodiments, the disease or disorder is a cancer, an autoimmune disorder, a genetic disease, an infectious disease, a neurological disease, an inflammatory disease, a metabolic disease or a combination thereof.

The compounds and compositions described herein, can be used to treat genetic disorders. For example, a nucleic acid molecule can be modulated and targeted by the compound.

In some embodiments, the method comprises administering a compound (e.g., having structures (I), (III), and/or (V)) comprising a pharmaceutically acceptable salt, hydrate, or solvate thereof Examples of cancers that can be treated by compounds comprising at least one neutralizing moiety having structure (V) include, but is not limited to, blood cancer (leukemia, lymphoma), bone cancer (osteosarcoma, chondrosarcoma), breast cancer (various carcinomas), eye cancer (melanoma, retinoblastoma), gastrointestinal cancer (hepatoma, bladder, colon, esophagial, pancreatic, stomach tumors), kidney, urinary tract and urethral cancer (renal carcinoma, urothelial carcinoma), muscular system cancer (rhabdomyosarcoma, fibrosarcoma), nervous system cancer (gliomas, astrocytomas, meningiomas, pituitary tumors, reproductive system cancer (testicular, prostate, cervical, endometrial, ovarian), respiratory system cancer (lung cancers, head and neck cancers), skin cancer (melanoma, basal cell carcinoma), and other cancers.

Examples of infectious diseases that can be treated by compounds comprising at least one neutralizing moiety having structure (V) include but is not limited to, chronic or latent viral infections (HIV, HCV (hepatitis C virus), HSV (herpes simplex virus), HTLV (human T-lymphotropic virus)), acute viral infections (Influenza, West Nile, Ebola), Bacterial (*Mycobacteria* spp., *Rickettsia* spp., *Brucella* spp), protozoan (*Leishmania* spp., *Chlamydia* spp., *Plasmodium* spp. Malaria) and others.

Examples of infectious diseases that can be treated by compounds comprising at least one neutralizing moiety having structure (V) include but is not limited to, alpha-1 antitrypsin deficiency (AATD), antiphospholipid syndrome (APS), autism, autosomal dominant polycystic kidney disease (ADPKD), Crohn's disease, Cystic Fibrosis, Down disease, Duchenne muscular dystrophy (DMD), Factor V Leiden thrombophilia, Gaudier disease, Hemophilia, Huntington's disease, Parkinson's disease, Wilson disease, polycystic kidney disease, Pelizaeus-Merzbacher disease, Vitelly-form Macular Dystrophy 2, and others.

Figure 3:
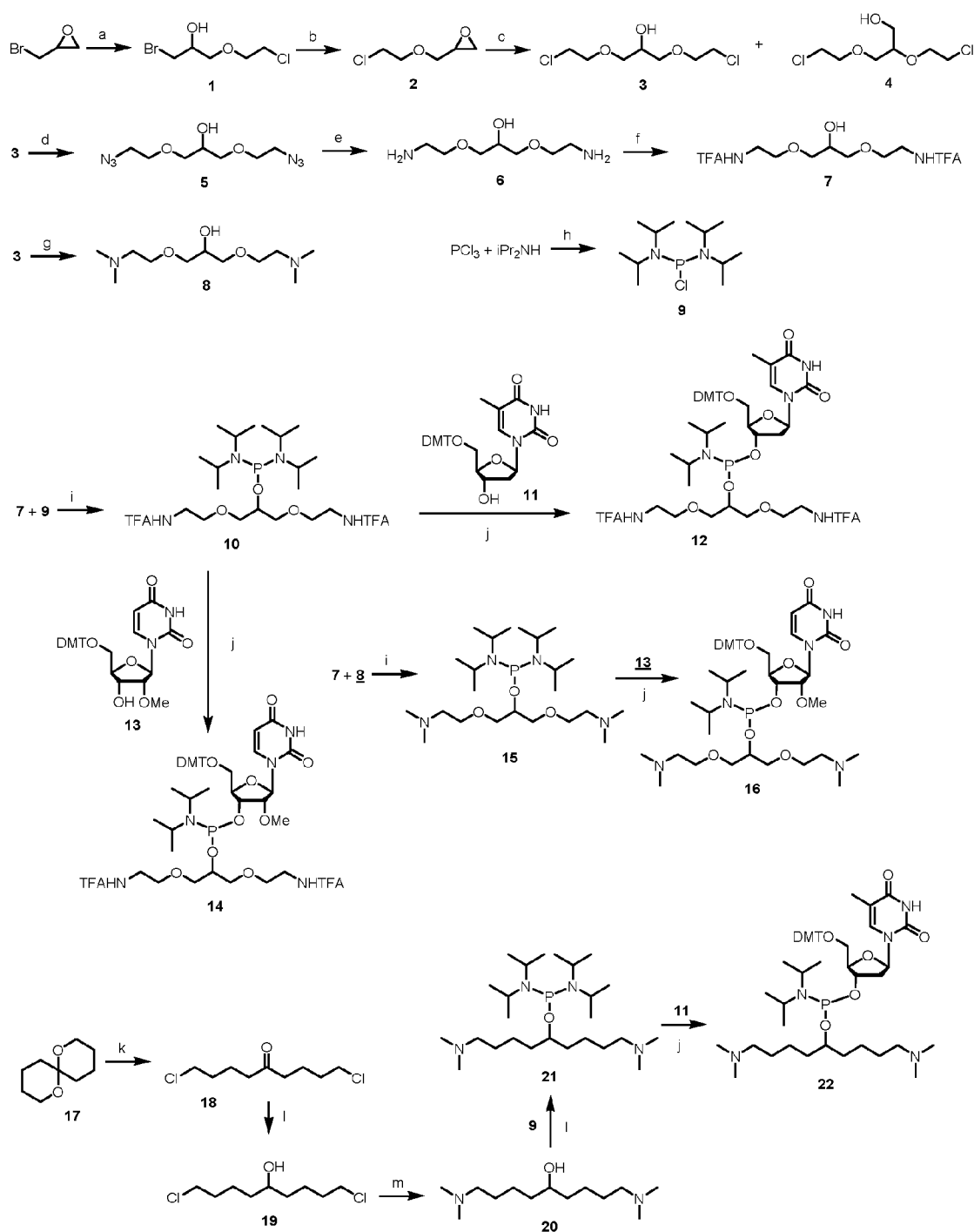
FIG. 3 illustrates a schematic synthesis to generate neutralizing moieties, phosphitylating agents and phosphoramidite monomers.

The compositions and compounds can be synthesized by the methods disclosed herein and illustrated in FIG. 3. One of ordinary skill in the art can readily appreciate different chemical approaches and synthetic schemes. The following examples, such as the synthesis of the compositions and compounds, and FIG. 3 are provided for illustrative purposes only and are in no way intended to limit the scope of the present invention.

EXEMPLIFICATION

Example 1: Synthesis of
1-Bromo-3-(2-Chloroethoxy)Propan-2-Ol
(Compound 1 in FIG. 3)

2-Chloroethanol (161 g, 134 ml, 2 mol) was dissolved in 60 ml anhydrous dichloromethane. Boron trifluoride etherate (1 ml) was added on stirring and the resulted solution was cooled, protected from moisture, to −4° C. Epibromohydrin (54.8 g, 34.2 ml, 0.4 mol) was added drop-wise during 35 min with stirring and cooling at −7 to −5° C. The clear solution was stirred for 3 hrs at 0° C. and then left to warm up to room temperature. The progress of the reaction was monitored by TLC (Petroleum ether/Ethyl acetate 2:1) and Hanessian's stain. Upon completion, the reaction mixture was evaporated under vacuum (12 mm Hg) in 45° C. bath to obtain 82.6 g (95%) of crude product which appeared as yellowish oil. According to $^1$H NMR, this material contained 10% (w/w) 2-chloroethanol. This product was used in the next step without further purification. Analytically pure material was obtained by vacuum distillation. $^1$H NMR (300 MHz, CDCl$_3$) δ: 3.99 (q, J=5.32 Hz, 1H), 3.79 (m, 2H), 3.65 (m, 4H), 3.53 (m, 2H), 2.42 (bs, 1H); $^3$C NMR (75 MHz, CDCl$_3$) δ: 72.38, 71.43, 69.87, 42.85, 34.81.

Example 2: Synthesis of
2-((2-Chloroethoxy)Methyl)Oxirane (Compound 2
in FIG. 3)

Crude 1-bromo-3-(2-chloroethoxy)propan-2-ol (82.6 g, 0.38 moles) was dissolved in dry tetrahydrofuran (150 ml). The solution was cooled on an ice bath. Tertiary potassium butoxide (1M solution in THF, 360 ml, 0.36 mol) was added drop-wise within 30 min on ice bath with cooling and stirring. The mixture was stirred for 1 hr on ice cooling and then was filtered under vacuum. The precipitate was washed with petroleum ether (2×150 ml). The combined filtrate and washings were evaporated under vacuum to oil. This oil was dissolved in ether (300 ml), and the solution was extracted with water (2×200 ml), filtered through a cotton plug, and evaporated under vacuum to give 37 g of crude 2-((2-chlorocthoxy)methyl)oxirane. This material was further purified by vacuum distillation at 0.1 mm Hg. After small (0.32 g) pre-run of 2-chloroethanol, the main fraction was distilled at 36-45° C. to give 28.0 g (57%) of pure 2-((2-chloroethoxy)methyl)oxirane. H NMR (300 MHz, CDCl$_3$) δ: 3.90-3.73 (m, 3H), 3.65 (m, 2H), 3.46 (dd, J$_1$=5.9 Hz, J$_2$=11.7 Hz, 1H), 3.18 (m, 1H), 2.82 (dd, J$_1$=4.2 Hz, J$_2$=5.0 Hz, 1H), 2.64 (dd, J$_1$=2.7 Hz, J$_2$=5.0 Hz, 1H); $^3$C NMR (75 MHz, CDCl$_3$) δ: 71.79, 71.32, 50.69, 43.97, 42.80.

Example 3: Synthesis of 1,3-Bis(2-Chloroethoxy)Propan-2-Ol (Compound 3 in FIG. 3)

Boron trifluoride etherate (0.415 ml) was added drop-wise with stirring to a cooled (−15-−10° C.) 2-chloroethanol (79.6 g, 66.0 ml, 0.988 mol). 2-((2-Chloroethoxy)methyl)oxirane (27 g, 0.198 mol) was added drop-wise during 30 min with stirring at the same temperature. The reaction mixture was kept at 0-5° C. for 3 hrs, and then concentrated under vacuum (12 mm Hg, 45° C. bath) to an oily liquid. This oil was dissolved in ethyl acetate (150 ml) and the solution was washed with 10% sodium carbonate (50 ml), saturated brine (50 ml), and filtered through a cotton plug. The solvent was evaporated on rotary evaporator (12 mm Hg, 45° C. bath). The residue was subjected to vacuum distillation to give 27.7 g (64.6%) distillate at 115-121° C. (0.1 mmHg). The $^1$H and $^3$C NMRs of this distillate revealed that it contains ca. 10% of the isomeric 2,3-bis(2-chloroethoxy)propan-1-ol (compound 4). It was purified from this isomer by flash chromatography on silica gel. Distillate (5.3) g was loaded on a silica gel cartridge (Agela Silica-CS, 120 g) and eluted with a gradient of ethyl acetate/petroleum ether 1:10 (EA/PE, 2 L) to EA/PE 2:1 (3 L). Fractions 5-32 (15 ml each) containing pure product were combined and evaporated to give 2.27 g of 1,3-bis(2-chloroethoxy)propan-2-ol appeared as colorless oil. Fractions 33-90 containing impure product were combined and evaporated and subjected to a second silica gel chromatography under the same conditions to give additional 0.72 g of pure product. The yield of purified product (compound) 3 was 36%. $^1$H NMR (300 MHz, CDCl$_3$) δ: 3.98 (m, 1H), 3.76 (m, 4H), 3.68-3.51 (m, 8H), 2.82 (d, J=4.3 Hz, 1H); $^3$C NMR (75 MHz, CDCl$_3$) δ: 72.05, 71.38, 69.34, 42.86.

Example 4: Synthesis of 1,3-Bis(2-Azidoethoxy)Propan-2-Ol (Compound 5 in FIG. 3)

1,3-Bis(2-chloroethoxy)propan-2-ol (8.76 g, 0.04 mol of crude distillate, containing ca. 10% of isomeric 2,3-bis(2-chloroethoxy)propan-1-ol), sodium azide (9.97 g, 0.153 mol) and sodium iodide (7.2 g, 0.048 mol) was stirred in 100 ml N,N-dimethylformamide for 16 hrs at 95-100° C. After the cooling, the mixture was filtered and the filtrate was evaporated under vacuum. The residue was dissolved in dichloromethane (250 ml) washed with water (4×150 ml), and evaporated under vacuum to give 8.5 g, 92% of crude product as a slightly yellow oil, containing ca. 10% of isomeric 2,3-bis(2-azidoethoxy)propan-1-ol. This material was purified in two portions by silica gel chromatography on Agela Silica-CS cartridges, 120 g. The elution was carried out with a gradient of ethyl acetate/petroleum ether from 1:10 to 1:2. The fractions containing pure material (TLC, Hanessian's stain) were combined and evaporated, to give, after drying on vacuum and at room temperature (RT), 5.2 g of pure compound 5, as light oil. The mixed fractions were evaporated and subjected to a second purification under the same conditions as described above to give additional 0.92 g of pure material. Total yield of pure product (compound) 5 was 6.12 g, 67%. $^1$H NMR (300 MHz, CDCl$_3$) δ: 4.00 (m, 1H), 3.72 (m, 4H), 3.66-3.55 (m, 4H), 3.41 (m, 4H), 2.48 (bs, 1H); $^3$C NMR (75 MHz, CDCl$^3$) δ: 72.05, 70.36, 69.31, 50.63.

Example 5: Synthesis of 1,3-Bis(2-Aminoethoxy)Propan-2-Ol (Compound 6 in FIG. 3)

A solution of triphenylphosphine (8.68 g, 33 mmol) in THF (8 ml) was added to a solution of compound 5 (3.05 g, 13.2 mmol) in THF (4 ml) under argon with stirring. The flask was equipped with a bubbler and cooled slightly, to maintain the reaction temperature below 30° C. After 5 hrs, the release of nitrogen was stopped. Water (0.65 ml) was added with stirring, and, again, the flask was cooled slightly to keep the temperature below 30° C. After 24 hrs, the reaction mixture was partially concentrated under vacuum (strong foaming was observed), and diluted with water (100 ml). After 30 min stirring, the white precipitate of triphenylphosphine oxide was filtered under vacuum and washed with water (3×20 ml). The combined filtrate and washings were evaporated under vacuum, to give, after drying on high vacuum at r.t., 2.36 g (100%) of product (compound) 6 as a clear oil. $^1$H NMR (300 MHz, CDCl$_3$) δ: 3.99 (m, 1H), 3.54 (m, 8H), 2.89 (t, J=5.2 Hz, 4H), 1.96 (bs, 5H). MS (ESI+) m/z: observed, 179.10; calculated for $C_7H_{19}N_2O_3^+$, 179.13.

Example 6: Synthesis of 1,3-Bis(2-((Trifluoroacetyl)Amino)Ethoxy)-Propan-2-Ol (Compound 7 in FIG. 3)

Methyl trifluoroacetate (6.77 g, 5.32 ml, 53 mmol) was added drop-wise to compound 6 (2.36 g, 13.2 mmol) with stirring on ice bath. The resulted solution was sealed overnight at room temperature. The volatiles were evaporated under vacuum, and the residue was purified on silica gel cartridge (Agela Silica-CS, 120 g) using ethyl acetate/petroleum ether 2:1. Fractions containing the product were evaporated. The residue was dissolved under argon in a mixture of anhydrous ether and toluene (30 ml of each), and then treated under argon with 30 g molecular sieves 3A in a septum sealed flask. After 3 hrs, the solution was removed by a syringe, and the molecular sieves were washed with 2×20 ml mixture of anh. ether/toluene 1:1. The washing was conducted under argon using the same syringe technique without unsealing the flask. The combined solution and washings were evaporated under vacuum to give, after drying under high vacuum at room temperature, 3.18 g (65%) of product (compound) 7 as a clear oil, which was stored under argon and protected from moisture. $^1$H NMR (300 MHz, CDCl$_3$) δ: 7.03 (bs, 1H), 3.99 (m, 1H), 3.66 (m, 4H), 3.63-3.49 (m, 8H), 2.66 (bs, 1H); $^3$C NMR (75 MHz, CDCl$_3$) δ: 157.42 (q, J=37.3 Hz), 115.80 (q, J=287.2 Hz), 71.95, 69.69, 69.20, 39.64.

Example 7: Synthesis of 1,3-Bis(2-(Dimethylamino)Ethoxy)Propan-2-Ol (Compound 8 in FIG. 3)

1,3-Bis(2-chloroethoxy)propan-2-ol (compound 3, 2.0 g, 9.2 mmol) was mixed with 24 ml of 40% (w/w) solution of dimethylamine in water, sealed, and stirred for 36 hrs at r.t. The reaction mixture was passed through 40 ml of Biorad AG MP-1M anion exchange resin in the OW form. The resin was eluted with water until the eluate became neutral. The eluates were evaporate under vacuum to give product (compound) 8 (2.3 g, 100% yield, contained 6% water) as a white semi-solid substance. Compound 8 was rendered anhydrous by dissolving in a mixture of dry toluene (60 ml), THF (40 ml), and acetonitrile (100 ml), while stirring for 3 hrs with molecular sieves 4A, filtering anaerobically, washing of the molecular sieves with 3×5 ml THF, followed by evaporation of the filtrate and washings under vacuum. $^1$H NMR (300 MHz, D$_2$O) δ: 3.89 (m, 1H), 3.60 (m, 4H), 3.46 (m, 4H), 2.82 (m, 4H), 2.43 (s, 12H); $^{31}$P NMR (75 MHz, D$_2$O, $^1$H dec.) δ: 71.68, 68.82, 66.39, 56.94, 43.53.

Example 8: Synthesis of 5'-O-(4,4'-Dimethoxytrityl)-2'-Deoxytymidine-3'-O—[O-((1,3-Bis(2-((Trifluoroacetyl)Amino)Ethoxy)-2-Propyl)Oxy)-N,N'-Diisopropylphosphoramidite] (Compound 12 in FIG. 3)

All procedures were conducted anaerobically under argon using syringe or cannula techniques. The glassware was flame-dried and cooled under argon. All solvents were absolute and septum sealed under argon or nitrogen.

A) Bis(diisopropylamino)chlorophosphine (Compound 9 in FIG. 3)

Diisopropylamine (3.92 g, 5.47 ml, 39 mmol, dried for 3 days under molecular sieves 3A) and dry toluene (20 ml) were loaded into a round bottom flask containing a teflon stirring bar. The flask was cooled in ice, and phosphorus trichloride (1.22 g, 0.78 ml, 8.88 mmol) was added dropwise with stirring at a rate slow enough to keep the temperature of the mixture below 10° C. The flask was equipped with a flame-dried and cooled under argon reflux condenser. The entire content was refluxed with stirring for 24 hrs. The reaction was controlled by $^{31}$P NMR in CDCl$_3$, which showed complete conversion of the PCl$_3$ singlet at 221.8 ppm to a multiplet at 142.9 ppm.

B) ((1,3-Bis(2-((trifluoroacetypamino)ethoxy)-2-propyl)oxy)-N,N,N',N'-tetraisopropylphosphordiamidite (Compound 10 in FIG. 3)

1,3-Bis(2-((trifluoroacetyeamino)ethoxy)propan-2-ol (7, 2.63 g, 7.10 mmol) was dissolved under argon in THF (10 ml) and added drop-wise with stirring to the reaction mixture from step A at −10-−15° C. After stirring for 2 hrs at −10° C., the reaction mixture was left to return to room temperature. The reaction was controlled by $^{31}$P NMR, which showed complete conversion of the multiplet at 142.9 ppm to a multiplet at 119.5 ppm. The reaction mixture was filtered by a cannula under argon pressure through a glass fiber filter (the filter was rendered dry by flashing with 50 ml of dry THF under argon). The reaction flask and the filtered solids were washed with dry THF (3×12 ml). The combined filtrate and washings were concentrated under vacuum in 25° C. bath to oil.

C) Compound 12 in FIG. 3 5'-O-(4,4'-Dimethoxytrityl) thymidine (compound 11, 2.22 g, 4.08 mmol) was dissolved in 6 ml of dry DMF and evaporated under vacuum (35° C. bath). The residue was dissolved under argon in 6 ml of dry DMF, and added under argon with stirring to the reaction mixture oil from step B. A solution of 5-ethylthiotetrasole solution in acetonitrile (0.45 M, 3 ml) was added with stirring. After 2 hrs at r.t., $^{31}$P NMR of the reaction mixture showed conversion of the multiplet at 119.5 to two multiplets (representing the two diastereomers of product (compound) 12) at 150.8 and 149.7 ppm, including byproducts at 151.4 (multiplet, di-((1,3-bis(2-((trifluoroacetyl)amino)ethoxy)-2-propyl)oxy)-N,N'-tetraisopropylphosphoramidite), and two doublets of multiplets at 17.1 and 7.7 ppm (H-phosphonate hydrolysis byproducts).

Triethylamine (0.5 ml) was added to the reaction mixture, and the volatiles were vacuum evaporated. The residue was dissolved in dichloromethane containing 1% triethylamine, loaded on a silica gel cartridge (Agela Silica-CS, 120 g), which was pre-equilibrated with 30% ethyl acetate, 1% triethylamine in petroleum ether, and eluted with a gradient of 30% ethyl acetate, 1% triethylamine in petroleum ether to 1% triethylamine in ethyl acetate. This resulted in partial purification of the product. The final purification was done on a preparative reverse phase resin column (100×300 mm). The fractions from the normal phase column containing the product were evaporated, dissolved in 1% triethylamine in methanol (15 ml), loaded on the column, and eluted with a gradient of 50% methanol, 1% triethylamine in water to 1% triethylamine in methanol for 50 min, and then isocratically with 1% triethylamine at methanol for 50 min at a flow rate of 100 ml/min. Fractions containing the product were pooled and evaporated under vacuum. LCMS, and $^{31}$P NMR analysis of this product showed that it contained ca. 17% of the corresponding amidate—a byproduct resulted from oxidation of the product during the reverse phase chromatography. This material was re-purified by the same chromatographic procedure with the following modifications: the mobile phases were chilled in ice and purged with helium for 3 hrs before and during the chromatography. Fractions containing compound 12 were pooled and evaporated under vacuum. The residue was evaporated from dry acetonitrile (2×150 ml) and finally from dry toluene to give 2.44 g (57%) of compound 12 as a white foam with 96% purity containing 4% of phosphoroamidate byproduct. Compound 12 consisted of 2 diastereomers in ratio 4:1% (from 1H, $^{31}$P NMR and HPLC). $^1$H NMR (300 MHz, C$_6$D$_6$) δ: 7.68, 7.59 (bs, 1H, 6-H), 7.58-6.73 (multiple m, 15, DMT Ar—H, CONH), 6.65 (dd, J$_1$=6.3 Hz, J$_2$=7.7 Hz, 0.8H, Diast.1 1'), 6.61 (dd, J$_1$=5.6 Hz, J$_2$=8.7 Hz, 0.2H, Diast.2 1'), 4.71 (m, 1H, H-3'), 4.44, 4.26 (m, 1H, H-4'), 4.11, 4.03 (m, 1H, (OCH$_2$)$_2$CHOP), 3.61-3.29 (multiple m, 14H, NHCH$_2$CH$_2$OCH$_2$, 5',5"), 3.334, 3.327 (s, 6H, OCH$_3$), 3.21, 3.10 (m, 2H, NCHMe$_2$), 2.35 (m, 2H, H-2',2"), 1.54, 1.53, 1.49 (s, 3H, dT-CH$_3$), 1.16, 1.12, 1.01 (d, J=6.8 Hz, 12H, NCHCH$_3$); 3'P NMR (121 MHz, C$_6$D$_6$) δ: 150.35 (m, $^1$H dec., s), 148.53 (m, $^1$H dcc., s). MS (ESI−) m/z: observed, 1042.18 (100.0%), 1043.19 (55.9%), 1044.18 (17.6%), 1045.16 (4.9%); calculated for C$_{48}$H$_{59}$F$_6$N$_5$O$_2$P [M−H], 1042.39 (100.0%), 1043.39 (54.9%), 1044.39 (18.2%), 1045.40 (3.6%). Retention times: Diastereomer 1, 6.44 min; Diastereomer 2, 6.67 min (Column, XBridge C18, 3 2.1×50 mm, mobile phases, A, 10 mM ammonium acetate pH 9, B, acetonitrile, gradient (% B in A) from 0% to 45% for 1 min, then to 100% for 5 min, and then isocratic 100% B for 1 min at 0.2 ml/min).

Example 9: Synthesis of 5'-O-(4,4'-Dimethoxytrityl)-2'-O-Methyluridine-3'-O—[O-(1,3-Bis(2-((Trifluoroacetyl)Amino)Ethoxy)-2-Propyl)-N,N'-Diisopropylphosphoramidite] (Compound 14 in FIG. 3)

Compound 14 was prepared using the procedure for compound 12, with the following modifications: in step A (preparing of compound 9), 5.39 g, 7.52 ml, 53 mmol diisopropylamine, 1.22 g, 0.78 ml, 8.88 mmol phosphorous trichloride, and 30 ml toluene were used; in step B (preparing of compound 10), 2.63 g, 7.10 mmol of compound 7 were used; and in step C, 3.28 g, 5.86 mmol of 5'-(4,4'-dimetoxytrityl)-2'-O-methyluridine (compound 13) were used. The purification was carried out directly on a 100×300 mm reverse phase resin column using helium de-gased and chilled in ice mobile phases. The product obtained after this purification step contained 17% of nucleoside (compound) 13, and was re-purified with the same column and procedure but with extended gradient step—from 50% methanol, 1% triethylamine in water to 1% triethylamine in methanol for 100 min. The product obtained after this re-purification was 2.76 g (44.4%). This material had 90% purity (H and $^{31}$P NMRs, LCMS) and contained 5% nucleoside (compound) 13, and 5% of methylphosphite resulted from a reaction of compound 14 with methanol from the mobile phase (replacing the diisopropylamino group of compound 14 by a methoxy group). Compound 14 consisted of 2 diastereomers in ratio 2:1% (from $_1$H, $_{31}$P NMR and HPLC). $^1$H NMR (300 MHz, C$_6$D$_6$) δ: 8.10, 7.95 (d, J=8.2 Hz, 1H, H-6), 7.62-6.95 (multiple m, 15, DMT Ar—H, CONH), 6.28 (d, J=4.5 Hz, 0.66H, Diast.1'), 6.13 (d, J=2.3 Hz, 0.33H, Diast.2 1'), 5.39, 5.35 (d, J=8.1 Hz, 1H, H-5), 4.74, 4.60 (m, 1H, H-2'), 4.50, 4.37 (m, 1H, H-3'), 4.25, 4.03 (m, 1H, (OCH$_2$)$_2$CHOP), 4.14 (m, 1H, H-4'), 3.70-3.27 (multiple m, 14H, NHCH$_2$CH$_2$OCH$_2$, 5',5"), 3.55, 3.49 (s, 3H, 2'-OMe), 3.377, 3.366, 3.347, 3.343 (s, 6H, DTM-OCH$_3$), 3.19, 3.11 (m, 2H, NCHMe2), 1.15, 1.02 (d, J=6.5 Hz, 12H, NCHCH$_3$); $^{31}$P NMR (121 MHz, C$_6$D$_6$) S 152.98 (m, H dec., s), 151.54 (m, $^1$H dec., s). MS (ESL) m/z: observed, 1058.12 (100%), 1059.08 (48.5%), 1060.07 (15.6%), 1061.04 (3.8%); calculated for C$_{48}$H$_{59}$F$_6$N$_5$O$_3$P— [M–H], 1058.38 (100.0%), 1059.38 (53.1%), 1060.38 (17.5%), 1061.39 (4.1%). Retention times: Diastereomer 1, 4.94 min; Diastereomer 2, 5.23 min (Column, XBridge C18, 3 μm, 2.1×50 mm, mobile phases, A, 10 mM ammonium acetate pH 9, B, acetonitrile, gradient (% B in A) from 0% to 60% for 1 min, then to 100% for 4 min, and then isocratic 100% B for 1 min at 0.2 ml/min).

Example 10: Synthesis of 5'-O-(4,4'-Dimethoxytrityl)-2'-O-Methyluridine-3'-O—[O-(1,3-Bis(2-((Dimethylamino)Ethoxy)-2-Propyl)-N,N'-Diisopropylphosphoramidite] (Compound 16 in FIG. 3)

Compound 16 was prepared using the procedure described for compound 12, with the following modifications: in step A (preparing of compound 9), 6.48 g, 9.04 ml, 64 mmol diisopropylamine, 1.47 g, 0.93 ml, 10.7 mmol phosphorous trichloride, and 30 ml toluene were used; in step B (preparing of compound 15), 2.30 g, 8.82 mmol of compound 8 were used; and in step C, 3.28 g, 5.86 mmol of 5'-(4,4'-dimetoxytrityl)-2'-O-methyluridine (compound 13) were used. The purification was carried out in two runs on a silica gel cartridge (Agela Silica-CS, 120 g) with a gradient of 3% triethylamine in ethyl acetate to 20% methanol and 3% triethylamine in ethyl acetate. Fractions containing the product were pooled, evaporated under vacuum (25° C. bath), and stripped from residual methanol by re-evaporation from dry acetonitrile containing 1% triethylamine to give, after drying on high vacuum, 3.50 g per run (7.0 g total, 71%) of compound 16 as a foam with 92% purity ($^1$H and $^{31}$P NMRs, LCMS). It contained 4.5% of the corresponding H-phosphonate (resulted from hydrolysis of the diisopropylamino group), 3% of the staring nucleoside (compound 13), and 1% of the corresponding phosphoroamidite (resulted from oxidation of compound 16). Compound 16 was a mixture of 2 diastereomers with ratio 53:47% (from $^1$H, $^{31}$P NMR and HPLC). $^1$H NMR (300 MHz, C$_6$D$_6$): 10.05 (bs, 2H, CONH), 8.16, 8.06 (d, J=8.2 Hz, 1H, H-6), 7.69-6.76 (multiple m, 12H, DMT Ar—H), 6.20 (d, J=1.8 Hz, 0.47H, Diast.1'), 6.17 (d, J=1.2 Hz, 0.53H, Diast.2 5.44, 5.38 (d, J=8.1 Hz, 1H, H-5), 4.89, 4.68 (m, 1H, H-2'), 4.51, 4.45 (m, 1H, H-3'), 4.37-4.21 (m, 1H, (OCH$_2$)$_2$CHOP), 4.24, 4.16 (m, 1H, H-4'), 3.78-3.45 (multiple m, 14, NHCH$_2$CH$_2$OCH$_2$, 5',5"), 3.65, 3.62 (s, 3H, 2'-OMe), 3.386, 3.369, 3.347, 3.340 (s, 6H, DTM-OCH$_3$), 2.67-2.47 (m, 2H, NCHMe$_2$), 2.24, 2.22, 2.19, 2.11 (s, 12H, NMe$_2$), 1.22, 1.19, 1.10 (d, J=6.7 Hz, 12H, NCHCH$_3$); $^{31}$P NMR (121 MHz, C$_6$D$_6$) δ: 153.29 (m, $_1$H dec., s), 151.47 (m, $_1$H dec., s). MS (ESL) m/z: observed, 922.19 (100%), 923.17 (50.7%), 924.12 (16.7%), 925.24 (2.9%); calculated for C$_{48}$H$_{69}$N$_5$O$_{11}$P— EM–H], 922.47 (100.0%), 923.48 (53.1%), 924.48 (16.1%), 925.48 (3.7%). Retention times: Diastereomer 1, 8.41 min; Diastereomer 2, 8.85 min (Column, XBridge C18, 3 μm, 2.1×50 mm, mobile phases, A, 10 mM ammonium acetate pH 9, B, acetonitrile, gradient (% B in A) from 0% to 35% for 1 min, then to 100% for 12 min, and then isocratic 100% B for 1 min at 0.2 ml/min).

Example 11: Synthesis of 1,9-Dichlorononan-5-One (Compound 18 in FIG. 3) from Olean 1,7-Dioxaspiro[5.5]undecane (olean, compound 17, 15 g, 97 mmol, Alfa-Aesar catalog no. B21664) was mixed with conc. HCl (38.7 ml) and the mixture was heated at 90° C. for 10 min under vigorous stirring. The mixture became quickly homogenous and darkened. After cooling down to r.t., the mixture was extracted with DCM (300 ml), and the DCM extract was washed with water (150 ml) and 8% sodium bicarbonate in water (150 ml), then dried overnight over anhydrous sodium sulfate, filtered and evaporated under vacuum to oil. This oil was subjected to vacuum distillation (0.1 mm Hg). Three fractions were collected: fraction 1, 56-113° C., fraction 2, 113-116° C., and fraction 3, above 116° C. Fraction 2 consisted of pure product (2.3 g, 11.3%). $^1$H NMR (300 MHz, CDCl$_3$) δ: 3.53 (t, J=6.2 Hz, 4H, ClCH$_2$), 2.45 (t, J=8.8, 4H, COCH$_2$), 1.83-1.66 (m, 8H); $^3$C NMR (75 MHz, CDCl$_3$) δ: 209.85, 44.83, 41.89, 32.11, 21.20.

Example 12: Synthesis of 1,9-Dichlorononan-5-One (Compound 18 in FIG. 3) from A-Valerolacone 6-Valerolacone (4.00 g, 3.71 ml, 30 mmol) was loaded in a flask equipped with a reflux condenser, thermometer, and magnetic stirrer. Dry THF (6 ml) was added under Ar. The mixture was cooled on ice and NaH (60% in mineral oil, 800 mg, 20 mmol) was added in portions within a couple of minutes. The cooling bath was removed and the mixture was warmed carefully with a dryer—exothermic reaction. The heating was turned on and the mixture was bought slowly to reflux. After reflux for 1.5 hrs, the mixture turned into frothing semi-solid state. Additional THF (6 ml) was added. Conc. HCl (8 ml) was added in portions causing a lot of frothing at the beginning. The mixture was reflux briefly, and then the reflux condenser was replaced by a straight one, and ca. 15 ml were distilled off. Conc. HCl (6 ml) was added again and the distillation was continued until the vapor temperature exceeded 100° C. The mixture (two layers) was cooled and evaporated on rotary evaporator until most of the HCl was evaporated and the salts crystallized. Conc. HCl (8 ml) was added once again, the mixture was refluxed vigorously for 20 min and cooled in ice. Salts crystallized again and a couple of milliliters of water were added to dissolve them. The mixture was extracted with 2×30 ml ether. The ether extract was dried with Na$_2$SO$_4$, filtered, and the ether was evaporated under vacuum.

The resulting oil was subjected to vacuum distillation (0.1 mm Hg). Three fractions were collected: fraction 1 (45-86°

C.), fraction 2 (86-160° C.), and fraction 3 (above 160° C.). Fraction 2 (1.4 g) contained the product along with other by-products. Silica gel chromatography of fraction 2 (Agela Silica-CS, 120 g, Ethylacetate/Petroleum Ether, gradient from 1:50 to 1:10) give 249 mg (5.9%) of pure product (compound) 18.

Example 13: Synthesis of 1,9-Dichloro-5-Nonanol (Compound 19 in FIG. 3)

Sodium borohydride (358 mg, 9.5 mmol) was added to ice bath-cooled mixture of 1,9-Dichlorononan-5-one (compound 18, 4.20 g, 20 mmol), methanol (4 ml) and water (2 ml) with vigorous stirring. After 30 min at 0-4° C. the reaction mixture was extracted with ethyl acetate (3×50 ml). The extract was dried over $Na_2SO_4$, filtered, and evaporated under vacuum to give product (compound) 19 (3.92 g, 92%) appeared as a clear oil. H NMR (300 MHz, $CDCl_3$) δ: 3.63 (m, 1H, CHOH), 3.57 (t, J=6.6 Hz, 4H, $ClCH_2$), 1.81 (m, 4H, $CH_2CH_2Cl$), 1.69-1.39 (m, 9H, $CH_2$, OH); $^3C$ NMR (75 MHz, $CDCl_3$) δ: 71.62, 45.16, 36.81, 32.74, 23.19.

Example 14: Synthesis of 1,9-Bis(Dimethylamino)-5-Nonanol (Compound 20 in FIG. 3)

1,9-Dichloro-5-nonanol (compound 19, 3.87 g, 18.8 mmol) was evaporated under vacuum from THE (50 ml) to remove any traces of ethyl acetate. The residue was mixed with dimethylamine (40% solution in water, 100 ml), sealed, and stirred at r.t. for 20 hrs. The mixture was diluted with water (200 ml) and extracted with 3×150 ml ether. The ether was removed under vacuum and the resulted oil was rendered anhydrous by evaporation from toluene (2×100 ml) to give 3.3 g of compound 20 (76%) product came out as clear oil. H NMR (300 MHz, $CDCl_3$) δ: 3.67 (m, 1H, CHOH), 3.49 (bs, 1H, OH), 2.32 (m, 4H, $CH_2NMe_2$), 2.22 (s, 12H, $NMe_2$), 1.77-1.46 (m, 12, $CH_2$); $^3C$ NMR (75 MHz, $CDCl_3$) δ: 71.07, 59.88, 45.50, 38.03, 28.10, 23.85.

Example 15: Synthesis of 5'-O-(4,4'-Dimethoxytrityl)Thymidine-3'-O—[O-(Bis-(4-(Dimethyamino)Butyl)Methyl)-N,N'-Diisopropylphosphoramidite] (Compound 22 in FIG. 3)

Compound 22 was prepared using the procedure described for compound 12, with the following modifications: in step A (preparation of compound 9) 4.30 g, 5.99 ml, 42 mmol diisopropylamine, 0.972 g, 0.62 ml, 7.08 mmol phosphorous trichloride, and 20 ml toluene were used; in step B (preparation of compound 21), 1.50 g, 6.51 mmol of compound 20 were used; and in step C, 3.85 g, 7.08 mmol of 5'-(4,4'-dimetoxytrityl)-thymidine (compound 11), and 3 mmol (6.6 ml of 0.45 M solution in acetonitrile) of ethylthiotetrazole were used. Also, in step B after filtration, dimethylamine (2 ml) was added, and then compound 20 was added as neat oil, and the mixture reacted at room temperature for 2.5 hrs.

A) Bis(diisopropylamino)chlorophosphine (Compound 9 in FIG. 3) Diisopropylamine (4.30 g, 5.99 ml, 42 mmol dried over molecular sieves 3A) and dry toluene (20 ml) was loaded into a flame dried and cooled under Ar round bottom flask containing an teflon stirring bar. The flask was cooled in ice under Ar and phosphorus trichloride (0.972 g, 0.62 ml, 7.08 mmol) was added drop-wise with stirring in ice bath within 1 min. The flask was equipped with a flame-dried and cooled under argon reflux condenser, and the content was refluxed with vigorous stirring for 20 hrs. The reaction was controlled by $^{31}P$ NMR in $C_6D_6$, which showed complete conversion of the $PCl_3$ singlet at 221.8 ppm to a multiplet at 132.3 ppm, and small amount (8%) of doublet of multiplets centered at 2.57 ppm, representing a hydrolysis product (H-phosphonate).

B) O-(bis-(4-(dimethyamino)butyl)methyl)-N,N,N',N'-tetraisopropylphosphordiamidite (Compound 21 in FIG. 3)

1,9-Bis(dimethylamino)-5-nonanol (20) (compound 20, 1.50 g, 6.51 mmol) was dried by vacuum evaporation from dry toluene (2×50 ml). Dry dimethylamine (2 ml, 1.43 g, 14 mmol) followed by compound 20 was added with stirring under Ar to the cooled (r.t.) reaction mixture from step A. The mixture was stirred for 2.5 hrs at r.t. and under Ar. The reaction was controlled by $^{31}P$ NMR in $C_6D_6$, which showed complete conversion of the multiplet at 132.3 ppm to a multiplet at 107.5 ppm. The reaction mixture was filtered by a cannula under argon pressure through a glass fiber filter (the filter was rendered dry by flashing with 50 ml of dry THE under argon). The reaction flask and the filtered solids were washed with dry THF (3×12 ml). The combined filtrate and washings were concentrated under vacuum (25° C. bath) to oil.

C) Compound 22 in FIG. 3 5'-O-(4,4'-Dimethoxytrityl) thymidine (compound 11, 3.85 g, 7.08 mmol) was dissolved in 50 ml of dry DMF and concentrated under vacuum (35° C. bath) to ¼ of its original volume. The resulted solution was added under argon with stirring to the reaction mixture oil from step B. A solution of 5-ethylthiotetrasole in acetonitrile (0.45 M, 6.6 ml) was added with stirring. After two hrs 15 min at r.t., $^{31}P$ NMR of the reaction mixture showed conversion of the multiplet at 107.5 to two multiplets (representing the two diastereomers of compound 22) at 144.7 and 144.1 ppm. Triethylamine (1 ml) was added to the reaction mixture and the volatiles were evaporated under vacuum. The residue was dissolved in a minimal amount of ethyl acetate containing 3% triethylamine, loaded on a silica gel cartridge (Agela Silica-CS, 120 g), which was pre-equilibrated with the same solvent, and eluted with a gradient of 3% triethylamine in ethyl acetate to 3% triethylamine in ethyl acetate/methanol 4:1. Fractions containing the product were pooled and evaporated under vacuum. The residue was evaporated from toluene (2×150 ml) and finally from dry toluene (50 ml) to give, after drying for 3 hrs at high vacuum, 4.95 g (77%) of compound 22 as a white foam with 96% purity containing 2% of phosphoroamiditc byproduct. Compound 22 consisted of 2 diastereomers with ratio 1:1% (from 1H, $^{31}P$ NMR and HPLC). $^1H$ NMR (300 MHz, $C_6D_6$) δ: 7.64-6.74 (mm, 14H, 6-H, DMT Ar—H), 6.65 (m, 1H, 1'), 4.77 (m, 11H, H-3'), 4.43, 4.29 (two m, 1H, H-4' of diast.1 and diast.2), 3.94, 3.80 (two m, 1H, $(OCH_2)_2CHOP$ of the two diastereomers), 3.68-3.29 (mm, 4H, 5',5", $NCHMe_2$), 3.35, 3.34 (s, 6H, $OCH_3$), 2.63-2.50 (mm, 2H, H-2',2"), 2.40 (t, J=7.2 Hz, 4H, $NCH_2$), 2.35 (s, 3H, dT-CH$_3$), 2.26, 2.23, 2.16, 2.11 (s, 12H, N(CH$_3$)$_2$, 1.76-1.39 (mm, 12H, CH$_2$), 1.22, 1.19, 1.15, 1.03 (d, J=6.9 Hz, 12H, NCHCH$_3$); $^{31}$P NMR (121 MHz, C$_6$D$_6$) δ:145.15 (m, $^1$H dec., s), 145.43 (m, $^1$H dec., s). MS (ESI$^+$) m/z: observed, 903.94 (100.0/%), 904.95 (40.9%), 905.90 (12.3%), 906.88 (2.6%); calculated for C$_{50}$H$_{75}$N$_5$O$_8$P [M+H]$^+$, 904.54 (100.0%), 905.54 (55.2%), 906.54 (17.6%), 907.55 (2.7%). Retention times: Diastereomer 1, 6.34 min; Diastereomer 2, 6.72 min (Column, XBridge C18, 3 μm, 2.1×50 mm, mobile phases, A, 10 mM ammonium acetate pH 9, B, acetonitrile, gradient (% B in A) from 0% to 35% for 1 min, then to 100% for 8 min, and then isocratic 100% B for 1 min at 0.2 ml/min).

Example 16: Synthesis of Oligonucleotides Containing Neutralizing Moieties at the Target Locations Compounds 12, 14, 16, and 22 shown in FIG. 3 allowed the incorporation of specific neutralizing moieties in the backbone of an oligonucleotide during the direct automated synthesis as demonstrated herein. Neutralizing moieties synthesized from compounds 12 and 14 are referred to as compound (i). Neutralizing moieties synthesized from compound 16 is referred to as compound (ii). Neutralizing moieties synthesized from compound 22 is refined to as compound (iii). Specific structures of compounds (i), (ii), and (iii) are illustrated in Table 1 below.

Phosporamidite synthones, such as compounds 12, 14, and 16 where used for the incorporation of one or more neutralizing moieties with primary or tertiary amines at the termini into the sugar-phosphate backbones of the oligonucleotide. Oligonucleotides were synthesized on a 394 DNA/RNA synthesizer (Applied Biosystems) using standard phosphoramidite chemistry and mild deprotection phosphoramidite monomers (Glen Research, Sterling, Va. or ChemGenes, Wilmington, Mass.). Coupling rates for new modified monomers were as good as that for standard phosphoramidites. As shown, a the variety of oligonucleotides (Table 2) and new monomers were compatible with phosphoramiditc chemistry.

For instance, the incorporation of FAM labeling groups at the 5'-positions of oligonucleotide, 6-Fluorescein Phosphoramidite (FAM) (Cat. #10-1964-90, Glen Research, Sterling, Va.) was used. For the incorporation of thiophosphatc segments, oxidation was performed by using Beaucage thiolation reagent. Oligonucleotides shown in Table 2 were purified on standard C18 HPLC columns by separating compounds with 4,4'-Dimethoxytrityl groups from other capped oligonucleotides. Deprotection of synthesized oligonucleotides were performed by 1 hr incubation of controlled porous glass (CPG; a solid support) with oligonucleotide in the mixture of concentrated ammonia: 40% methylamine. MWs of the synthesized oligonucleotide were determined by mass spec (MS) analysis. Excellent correlation between the calculated and MW determined by mass spectrometry was demonstrated shown in Table 3, below.

TABLE 1

Structures of Compounds (i), (ii) and (iii) (e.g., neutralizing moiety) derived from compounds 12, 14, 16, and 22 onto the backbones of oligonucleotides during automated synthesis

| Structure of Neutralizing Moiety (NM) | Compound ID |
|---|---|
| [Structure: NH$_2$+ CH$_2$CH$_2$-O-CH$_2$-CH(O-)-CH$_2$-O-CH$_2$CH$_2$ NH$_2$+] | Compound (i): 1,3-Bis(2-aminoethoxy)propan-2-ol |
| [Structure: (CH$_3$)$_2$NH+ CH$_2$CH$_2$-O-CH$_2$-CH(O-)-CH$_2$-O-CH$_2$CH$_2$ NH+(CH$_3$)$_2$] | Compound (ii): 1,3-Bis(2-(dimethylamino)ethoxy)propan-2-ol |
| [Structure: (CH$_3$)$_2$NH+ (CH$_2$)$_4$-CH(O-)-(CH$_2$)$_4$ NH+(CH$_3$)$_2$] | Compound (iii): 9-Bis(dimethylamino)-5-nonanol |

TABLE 2

Sequences of Oligonucleotides with Neutralizing Moieties Synthesized and Tested

| SEQ ID NO: | Sequence (5'-3') | Chemistry: Compound ID (table 1); neutralization (%) |
|---|---|---|
| 1 (ZT1) | ATA GTA GTA GTC CTA GTC T | DNA—P=O[a] (i); 16 |
| 2 (ZT2) | ATA GTA GTA GTC CTA GTC T | DNA—P=O (i); 33 |
| 3 (ZT3) | ATA GTA GTA GTC CTA GTC T | DNA—P=O (i); 50 |
| 4 (ZT4) | UUC GUA GUU GUC UUA GUC C | 2'OMe—P=O[b] (NA); 0 |
| 5 (ZT5) | UUC GUA GUU GUC UUA GUC C | 2'OMe—P=O[b] (i); 33 |
| 6 (ZT6) | UUC GUA GUU GUC UUA GUC C | 2'OMe—P=O (i); 50 |
| 7 (ZT7) | UUC GUA GUU GUC UUA GUC C | 2'OMe—P=O (i); 100 |
| 8 (ZT8) | FAM-UUC GUA GUU GUC UUA GUC C | 2'OMe—P=O (NA); 0 |
| 9 (ZT9) | FAM-UUC GUA GUU GUC UUA GUC C | 2'OMe—P=O (i); 15 |
| 10 (ZT10) | FAM-UUC GUA GUU GUC UUA GUC C | 2'OMe—P=O (i); 95 |
| 11 (ZT11) | UCG UAC UUA UCU UAA UCC UAC | 2'OMe—P=O (ii); 90 |
| 12 (ZT12) | UCG UAC UUA UCU UAA UCC UAC | 2'OMe—P=O (ii); 60 |
| 13 (ZT13) | UCG UAC UUA UCU UAA UCC UAC | 2'OMe—P=O (ii); 30 |
| 14 (ZT14) | UCG UAC UUA UCU UAA UCC UAC | 2'OMe—P=O (ii); 15 |
| 15 (ZT15) | UCG UAC UUA UCU UAA UCC UAC | 2'OMe—P=O |
| 16 (ZT16) | GCG UAG GAU UAA GAU AAG UAC | NA; 0 |
| 17 (ZT17) | FAM-UCG UAC UUA UCU UAA UCC UAC | |
| 18 (ZT18) | FAM-UCG UAC UUA UCU UAA UCC UAC | 2'OMe—P=O (ii); 28 |
| 19 (ZT19) | FAM-UCG UAC UUA UCU UAA UCC UAC | 2'OMe—P=O (ii); 56 |
| 20 (ZT20) | FAM-UCG UAC UUA UCU UAA UCC UAC | 2'OMe—P=O (ii); 86 |
| 21 (ZT21) | CAC AAA AUC GGU UCU ACA GGG UA | 2'OMe—P=S[c] NA; 0 |
| 22 (ZT22) | CAC AAA AUC GGU TCU ACA GGG UA | 2'OMe—P=S (ii); 55 |
| 23 (ZT23) | CUG UGG AAG UCU A | 2'OMe—P=O (ii); 50 |
| 24 (ZT24) | CUG UGG AG UCU A | 2'OMe—P=S NA; 0 |
| 25 (ZT25) | AGA CTA GGA CTA CTA CTA TT | 2'OMe—P=S NA; 0 |
| 26 (ZT26) | CAC AAA AUC GGU TCU ACA GGG UA | 2'OMe—P=S (ii); 27 |

TABLE 2-continued

Sequences of Oligonucleotides with Neutralizing Moieties Synthesized and Tested

| SEQ ID NO: | Sequence (5'-3') | Chemistry: Compound ID (table 1); neutralization (%) |
|---|---|---|
| 27 (ZT27) | A<u>T</u>A GTA G<u>T</u>A G<u>T</u>C CTA G<u>T</u>C T | 2'OMe—P═O (i); 67 |
| 28 (ZT28) | FAM-CAC AAA A<u>U</u>C GG<u>U</u> UC<u>U</u> ACA GGG <u>U</u>A | 2'OMe—P═O (ii); 55 |
| 29 (ZT29) | FAM-CAC AAA AUC GGU TCU ACA GGG UA | 2'OMe—P═S NA; 0 |
| 30 (ZT30) | FAM-U<u>U</u>C GUA G<u>U</u>U G<u>U</u>C U<u>U</u>A G<u>U</u>C C | 2'OMe—P═O (i); 79 |
| 31 (ZT31) | ATA GTA GTA GTC CTA GTC T | DNA—P═O (NA); 0 |

$^a$DNA—P═O indicates deoxy-oligonucleotide with phosphate backbones.
$^b$2'OMe—P═O indicates 2'OMe derivative of RNA with phosphate backbones.
$^c$2'OMe—P═S indicates 2'OMe derivative of RNA with thiophosphate backbones.
NA = not applicable.
FAM = a fluorescein label.

In the sequences provided in Table 2, above. Underlined bases (e.g., U, T) indicates a location of a neutralizing moiety having the structure of compound (i); bases with a double underline (e.g., U, T) indicates a location of a neutralizing moiety having the structure of compound (ii).

In Table 2 above, Compound 12 (see FIG. 3) was used to synthesize SEQ ID NOS: 1-3 and 27. Compound 14 was used to synthesize SEQ ID NOS:5-7, 9, 10 and 30. Compound 16 was used to synthesize SEQ ID NOS: 11-14, 18-23, 26 and 28. SEQ ID NOS:4, 8, 15-17, 24-25, 29 and 31 were used as controls.

TABLE 3

Calculated and Actual Molecular Weights determined by mass spectrometry (MS).

| SEQ ID NO: | Calc. MW | MW by MS |
|---|---|---|
| 1 (ZT1) | 5975.2 | 5874.7 |
| 2 (ZT2) | 6135.3 | 6135.6 |
| 3 (ZT3) | 6295.4 | 6295.9 |
| 4 (ZT4) | 6217.1 | 6217.6 |
| 5 (ZT5) | 6377.7 | 6377.3 |
| 6 (ZT6) | 6698.1 | 6697.3 |
| 7 (ZT7) | 7177.8 | 7178.9 |
| 8 (ZT8) | 6754.2 | 6754.6 |
| 9 (ZT9) | 6914.3 | 6914.6 |
| 10 (ZT10) | 7714.9 | 7715.7 |
| 11 (ZT11) | 8104.3 | 8106.0 |
| 12 (ZT12) | 7671.9 | 7672.8 |
| 13 (ZT13) | 7239.5 | 7240.6 |
| 14 (ZT14) | 7023.3 | 7024.2 |
| 15 (ZT15) | 6807.2 | 6807.9 |
| 16 (ZT16) | 7075.3 | 7076.0 |
| 17 (ZT17) | 7374.3 | 7375.4 |
| 18 (ZT18) | 7806.7 | 7807.8 |
| 19 (ZT19) | 8239.0 | 8240.7 |
| 20 (ZT20) | 8671.4 | 8673.5 |
| 21 (ZT21) | 8023.9 | 8026.8 |
| 22 (ZT22) | 8889.6 | 8891.5 |
| 23 (ZT23) | 4945.9 | 4946.7 |
| 24 (ZT24) | 4512.5 | 4513.6 |
| 25 (ZT25) | | NA |
| 26 (ZT26) | | NA |
| 27 (ZT27) | | NA |
| 28 (ZT28) | | NA |
| 29 (ZT29) | | NA |
| 30 (ZT30) | | NA |
| 31 (ZT31) | | NA |

Example 16: Preservation of Watson-Crick Hybridization Properties

As it is shown herein in Table 3, melting temperatures (MT) of duplexes regardless of the number of charge neutralizing moieties with primary amines remain unchanged within the sensitivity of the method (rows 1 to 3). Melting was performed for 0.2 μM duplex in buffer with composition: 10 mM MgCl$_2$, 15 mM KCl, 25 mM HEPES, pH 7.3 with heating rate 0.5 deg/min. Increasing of the MT was observed for duplexes containing high number of charge neutralizing moieties what can be explained by their higher hydrophobicity (rows 7 to 10). As it is seen in rows 5 and 11, no melting was detected when oligonucleotides with BCG (both with primary and with tertiary amino groups) were mixed with 20-mer 2'OMe scramble sequence. This clearly indicates the absence of non-standard inter-molecular aggregation.

TABLE 4

Melting temperature (MT) of the duplexes containing different number and type of Neutralizing Moiety (NM)

| # | Duplexes | # of NM | MT (°C.) |
|---|---|---|---|
| 1 | ZT31:ZT25 | 0 | 55.2 |
| 2 | ZT1:ZT25 | 1 | 55.9 |

TABLE 4-continued

Melting temperature (MT) of the duplexes containing different number and type of Neutralizing Moiety (NM)

| # | Duplexes | # of NM | MT (° C.) |
|---|---|---|---|
| 3 | ZT2:ZT25 | 2 | 55.4 |
| 4 | ZT27:ZT25 | 4 | 56.4 |
| 5 | ZT27:Scrambled ON | 4 | No melting |
| 6 | ZT15:ZT16 | 0 | 56.2 |
| 7 | ZT14:ZT16 | 1 | 56.5 |
| 8 | ZT13:ZT16 | 2 | 57.5 |
| 9 | ZT12:ZT16 | 4 | 61.2 |
| 10 | ZT11:ZT16 | 5 | 67.2 |
| 11 | ZT11: Scrambled ON | 5 | No melting |

Example 17: Stability of Oligonucleotides

Stability of some oligonucleotides from the Table 2 was tested at high and low pH (3 to 12) and in serum. During the purification stage, compounds were incubated in concentrated ammonia for over 1 hr and later in 70% acetic acid for 15 min. All compounds from Table 2 were exposed to a pH ranging from 3 to 12 and didn't decompose. Compounds ZT11 and ZT12 were dissolved in PBS and stored at room temperature. HPLC analysis revealed no decomposition after a month of storage.

For the evaluation of stability of the same compounds in serum, ZT11 and ZT12 were dissolved in PBS and each was mixed with ZT15 (the same 2'OMe oligonucleotides with no neutralizing moiety). Both oligonucleotide mixtures were diluted (1:9) with bovine 20 serum. 2 mL reaction mixture with final 2 o.u. concentrations of oligonucleotide (each) was incubated at 37° C. Aliquotes of 250 µL were removed at zero, 2, 4, and 8 hrs, diluted with 2 mL of water, and subjected to solid phase extraction with C18 Glen-Pak cartridges (Glen Research). Captured oligonucleotides were eluted with 20% acetonitrile in water and the eluates were evaporated on a speed-vac. Resulted mixtures of oligonucleotides were analyzed on C18 HPLC column and Waters Alliance HPLC system (Waters Corporation). Initially, ratios between ZT15:ZT11 and ZT15:ZT12 were approximately 1:1. At the 8 hrs time point, the ratios became 1:12 and 1:10, respectively. The data clearly indicated that incorporation of neutralizing moieties in the oligonucleotide does not compromise the stability of oligonucleotide and significantly increases their stability in nuclease-containing biological fluids.

Example 18: Toxicity

Cytotoxicity of 2'OMe oligonucleotides containing different numbers of neutralizing moieties (terminated with both primary and tertiary amino groups) was evaluated in four different cell lines. 2'OMe oligonucleotide without neutralizing moieties were used as controls.

TABLE 5

Oligonucleotides and cell lines used for cytotoxicity determination

| Cell Line | Oligonucleotide tested (concentration in µM) | Observation time (hrs) |
|---|---|---|
| HEK293 | ZT4, ZT5, ZT6 (1, 10) | Up to 24 |
| A172 | ZT11-ZT15 (1, 5, 10) | Up to 96 |
| MCF7 | | |
| HeLa | | |

Large set of experiments demonstrated that the addition of neutralizing moieties did not increase the cytotoxicity regardless of their numbers. List of oligonucleotide and cell lines used are shown in Table 4. Effect of oligonucleotide comprising neutralizing moieties was compared to that of standard 2'OMe oligonucleotides at concentrations of 1 and 10 µM with untreated cells serving as an additional control. Relative viability of cells in each test condition was determined as the ratio of propidium iodide positive (apoptotic cells) to total cell numbers (Hoechst 33342 positive cells). Cytotoxicity was also determined visually by assessing basic cell/monolayer morphology. Viability data for HEK293 cells are presented in FIGS. 4A-4B, 5A-5D, and 6A-6D.

Figures 4A, 4B:
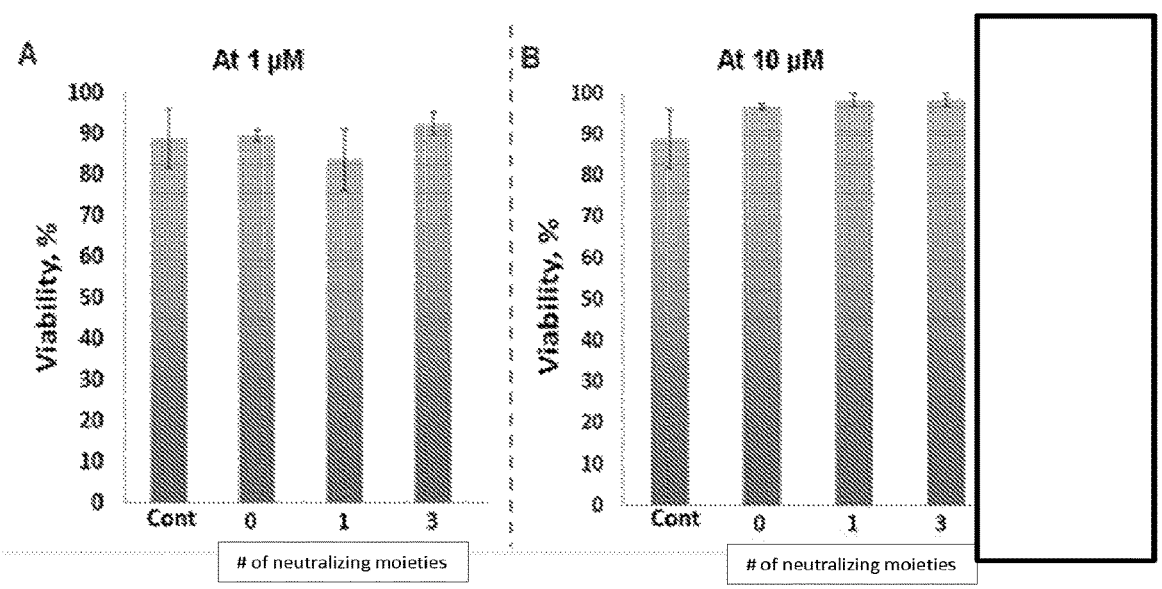
FIGS. 4A-4B illustrate the viability of HEK293 cells after 24 hour incubation with an oligonucleotide containing 0, 1, and 3 neutralizing moieties (SEQ ID NO:4, SEQ ID NO:5 and SEQ ID NO:6; ZT4, ZT5, and ZT6, respectively) at a concentration of 1 μM (FIG. 4A), and 10 μM (FIG. 4B).
Figure 5A:
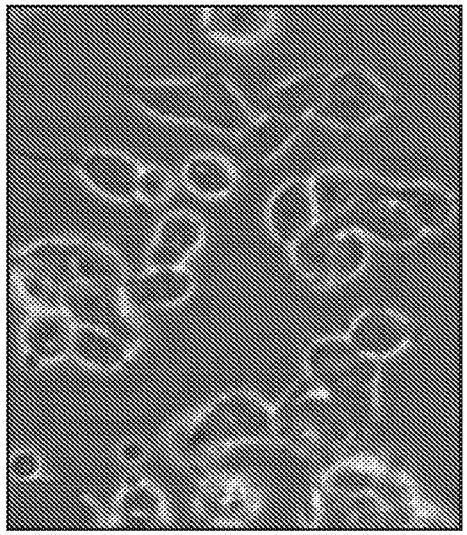
FIGS. 5A-5D illustrate phase-contrast images of the morphology of HEK293 cells in the presence of 1 μM oligonucleotide. Control cells (FIG. 5A) and cells treated with SEQ ID NO:4 (ZT4.
Figure 5B:
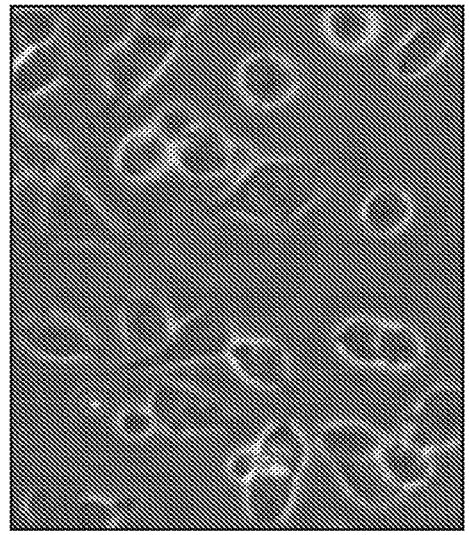
Figure 5C:
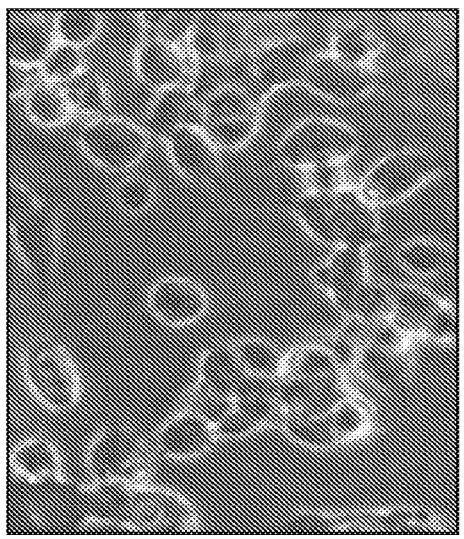
Figure 5D:
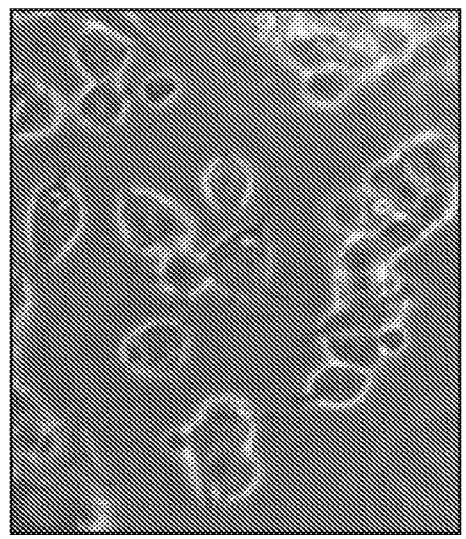
Figure 6A:
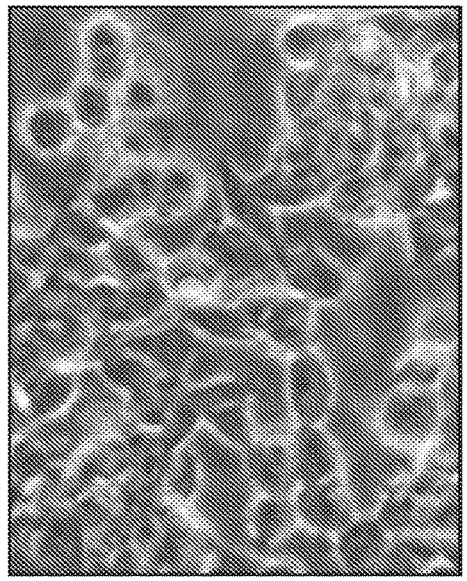
FIGS. 6A-6D illustrate phase-contrast images of the morphology of HEK293 cells in the presence of 10 μM oligonucleotide. Control cells (FIG. 6A) and cells treated with SEQ ID NO:4 (ZT4.
Figure 6B:
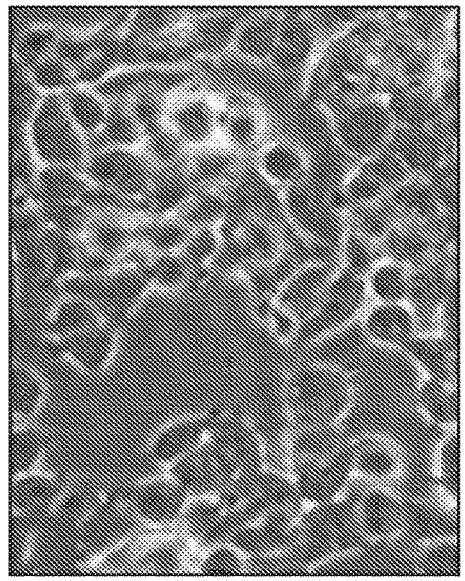
Figure 6C:
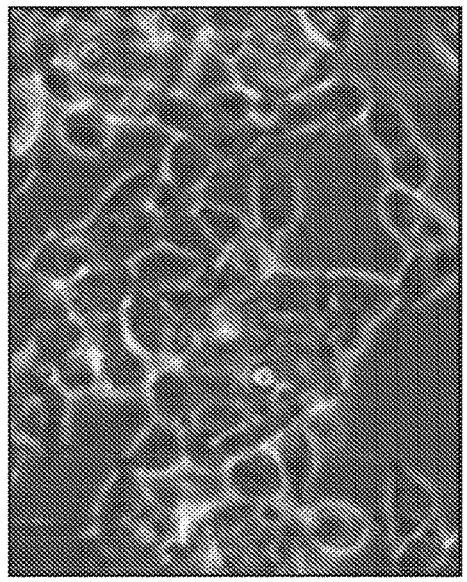
Figure 6D:
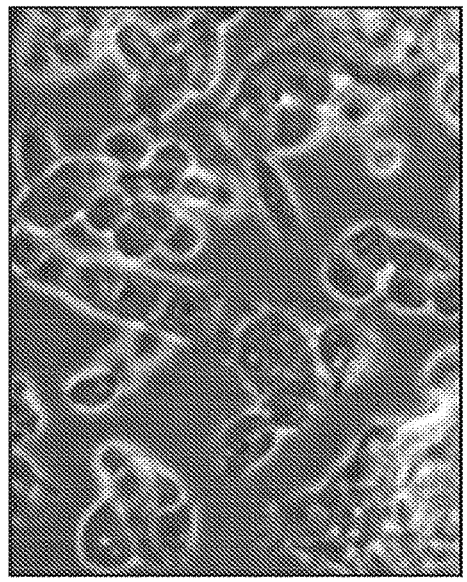

No visible effects of oligonucleotide on HEK293 were observed during the incubation for up to 24 hrs and for A172, HeLa, and MCF7 cells for up to 96 hrs. Average cell viability for HEK293 was 88%-98%, with no significant differences in viability between the untreated cells and any of the oligonucleotide-treated cells (FIGS. 4A-4B).

Figure 7A:
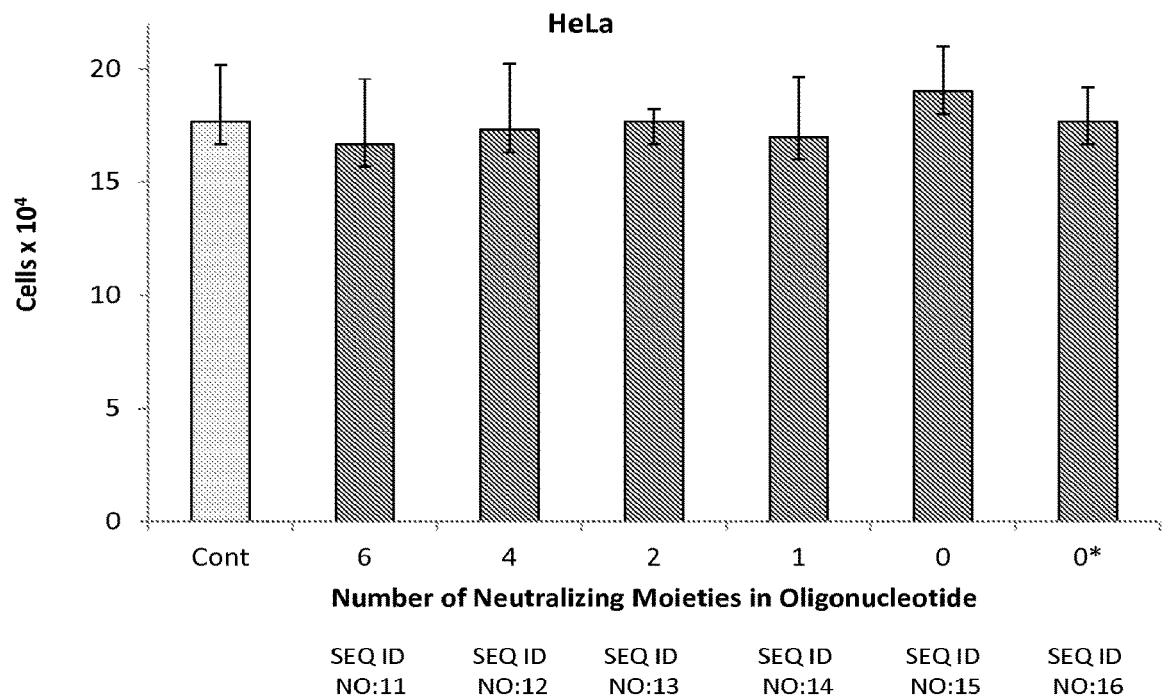
FIGS. 7A-7C illustrates the viability of HeLa (FIG. 7A), MCF7 (FIG. 7B), and A172 (FIG. 7C) cells incubated with 10 μM oligonucleotide having different numbers of neutralizing moieties indicated on the x-axis (corresponding to SEQ ID NOS:11-16; ZT11-ZT16). Cells were counted after 96 hrs.
Figure 7B:
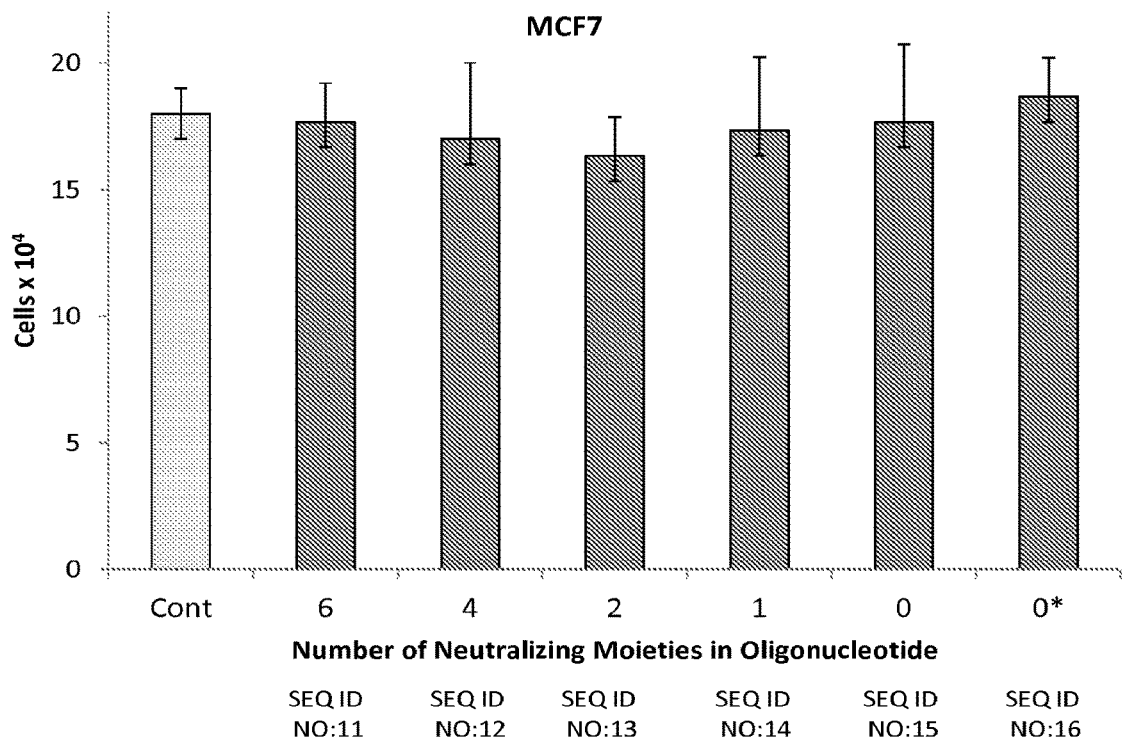
Figure 7C:
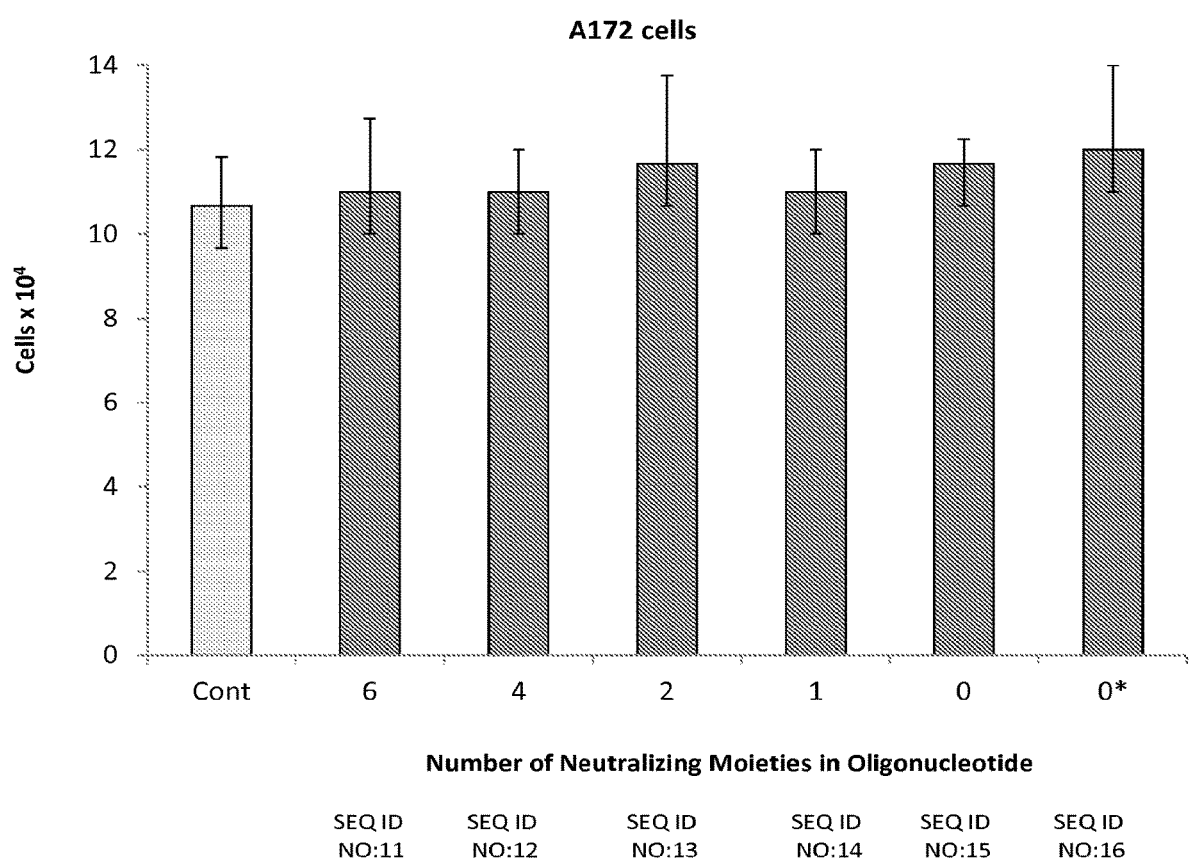
Figure 8A:
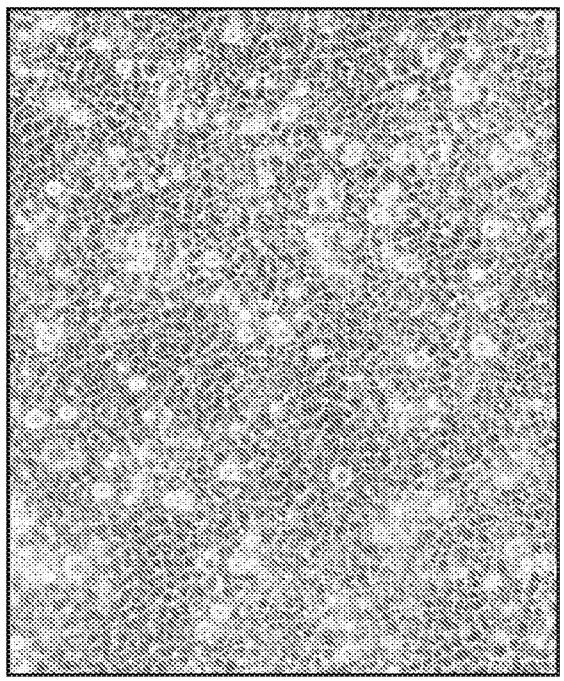
FIGS. 8A-8B illustrates phase-contrast images at 40× of HeLa cells treated with 10 μM oligonucleotide comprising 0 (SEQ ID NO:15; ZT15) (FIG. 8A) and 4 neutralizing moieties (branched chemical groups) (SEQ ID NO:12; ZT12) (FIG. 8B).
Figure 8B:
Figure 8C:
FIGS. 8C-8D illustrates phase-contrast images at 40× of MCF7 cells treated with 10 μM oligonucleotide comprising 0 (SEQ ID NO:15; ZT15) (FIG. 8C) and 4 neutralizing moieties (branched chemical groups) (SEQ ID NO:12; ZT12) (FIG. 8D).
Figure 8D:
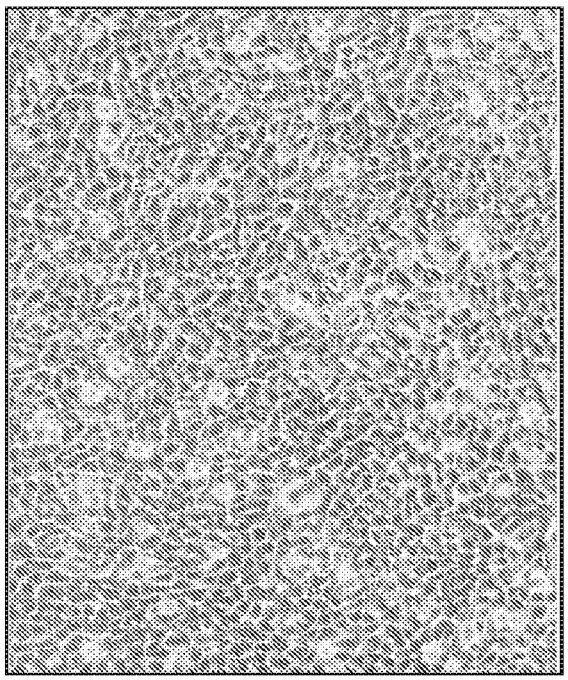

These results are supported by the visual toxicity data (FIGS. 5A-5D and 6A-6D), indicating that the compounds with different degrees of backbone neutralization with neutralizing moieties containing primary amino groups at the termini are not toxic to cells at concentration as high as 10 µM. Similarly, average cell viability for A172, MCF7, and HeLa cells was over 95% with no significant differences in viability between the untreated cells and the cells treated with neutralizing moiety containing oligonucleotides. Viability data for A172, HeLa, and MCF7 cells are illustrated in FIGS. 7A-7C and 8A-8B. These data confirmed that oligonucleotide with backbone neutralized from 14% to as high as 80% (ZT11) with neutralizing moieties containing tertiary amino groups at the termini are not toxic to cells at concentrations as high as 10 µM. Referring to FIG. 7A-7C: "Cont" stands for control i.e. no-oligonucleotide-treatment; * indicates a second control using an oligonucleotide with no neutralizing moieties.

Example 19: Effect of Charge Neutralizing Moiety Modifications on Cellular Uptake The effectiveness of the delivery of oligonucleotide comprising neutralizing moieties into the cytosol of cultured anchorage-dependent cells was studied with three cell lines. All three were developed from human tumors and represent epithelial (HeLa and MCF7) and mesenchymal (A172) cells. All oligonucleotides were labeled with 6-FAM (6-carboxyfluorescein) at 5'-terminus. Cells were grown in DMEM/10% FBS (no antibiotics) were plated on 24- or 96-well plates at a dilution which allows formation of a near-complete monolayer at 18-24 hrs after the plating. Alternatively, cells were cultured on glass cover slips placed in 60-mm dishes. Test samples dissolved in DMEM/0.5% FBS were added and cells were incubated at 37° C. in a CO2 incubator for a fixed period of time. At the end of incubation, cells were washed several times, fixed or lysed where necessary, and the amount of cell-associated fluorescence was measured using a plate reader or fluorescent microscope.

Figure 9A:
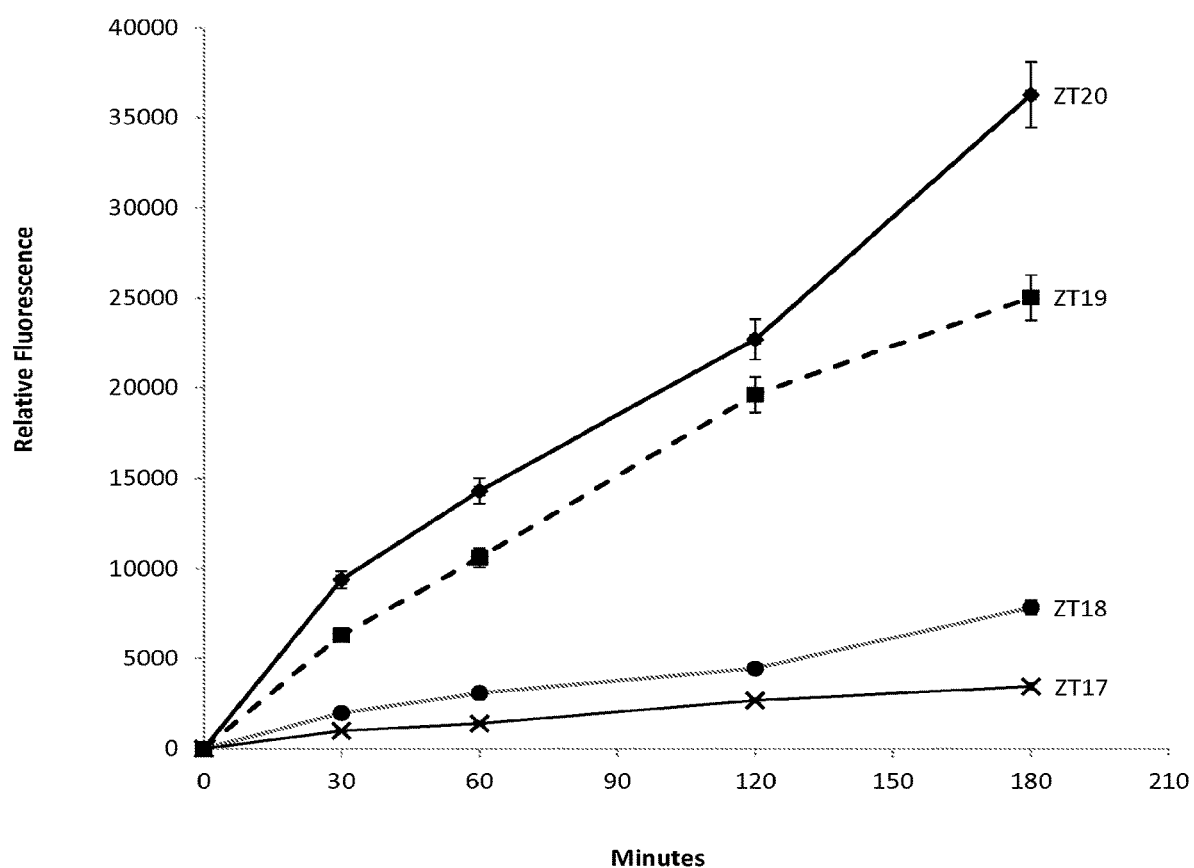
FIG. 9A illustrates penetration kinetics in MCF cells of various oligonucleotides (ZT17-ZT20 corresponding to SEQ ID NOS:17-20) with neutralizing moieties having tertiary amino groups at the terminal ends.
Figure 9B:
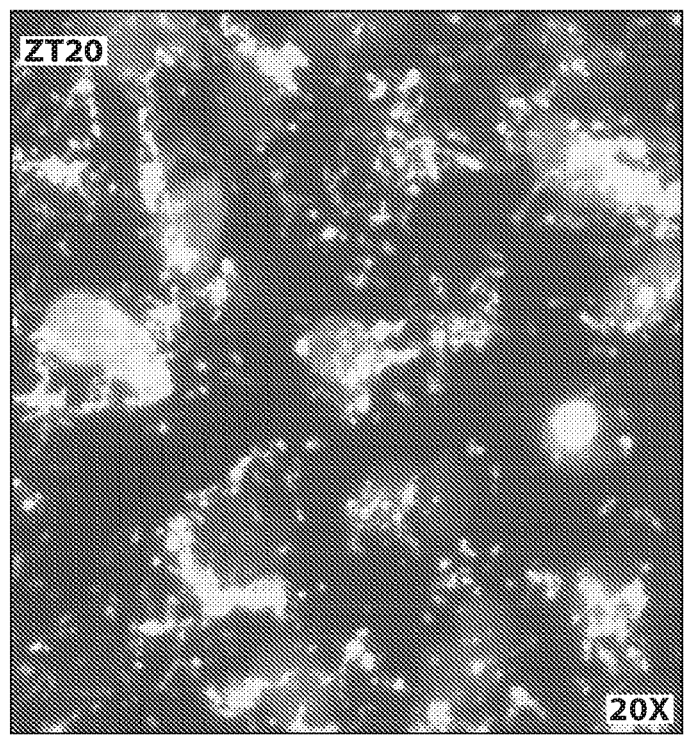
FIGS. 9B-9C illustrates fluorescent microscopy images of the uptake of oligonucleotides having SEQ ID NO:20 (ZT20.
Figure 9C:
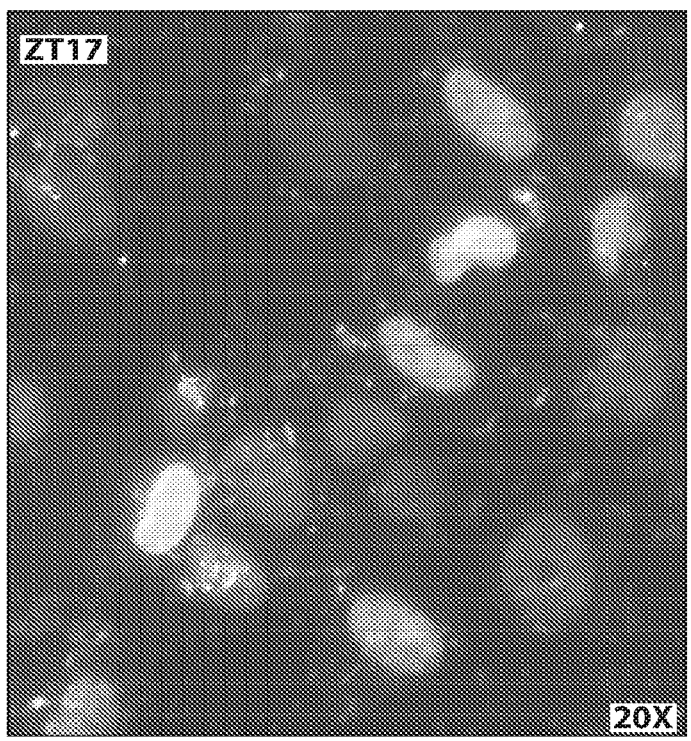

Oligonucleotide at a final concentration of 1 μM was added to near confluent cells without any formulation or cellular uptake enhancers. Kinetics were evaluated at 30, 60, 120, and 180 minute time points. As shown in FIG. 9A, significant increase of cellular penetration (3-4 times) was demonstrated for oligonucleotide comprising neutralizing moieties, and this increase was proportional to the number of neutralizing moieties in the oligonucleotide. For the visualization of cellular penetration, fluorescent images of A172 glioma cells treated with ZT17 (FIG. 9C) and ZT20 (FIG. 9B) for 150 min. and counterstained with DAPI. Bright spots correspond to the oligonucleotides labeled with 6-carboxyfluorescein (FAM).

Figure 9D:
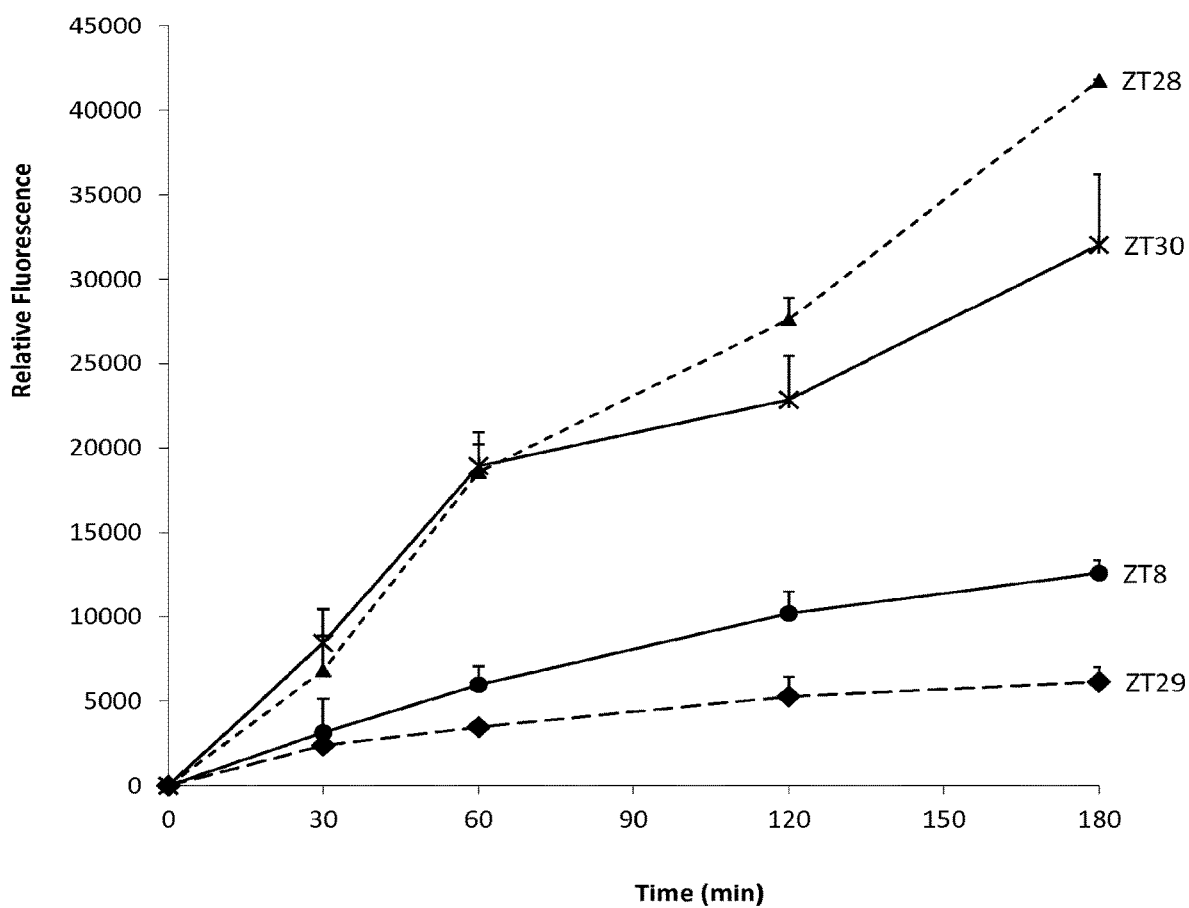
FIG. 9D illustrates the uptake in A172 cells of various oligonucleotides with different neutralizing moieties.

Hydrophobicity added by introducing neutralizing moieties also plays very important role in the enhancement of cellular uptake (FIG. 9D). Neutralizing moieties with tertiary amino groups at the termini (see FIGS. 2A-2E for structures) provide even higher penetration rate than neutralizing moieties with primary amino groups. As illustrated in FIG. 9D, oligonucleotide (ZT28) with four neutralizing moieties comprising tertiary amino groups penetrates more efficiently than an oligonucleotide with 5 neutralizing moieties (ZT30) containing primary amino groups. The poor kinetics of penetration in control oligonucleotides ZT29 and ZT8 (i.e., oligonucleotides without neutralizing moieties) are also illustrated.

Figure 10A:
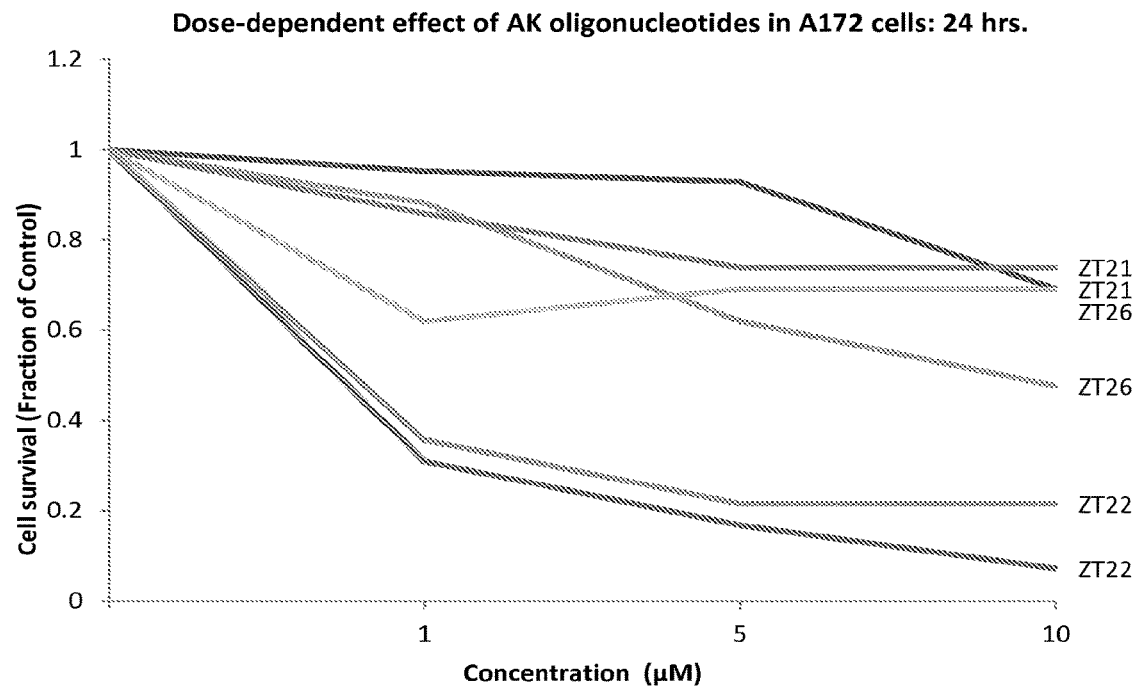
FIGS. 10A-10C illustrates the fraction of viable A172 cells using 1, 5, and 10 μM of oligonucleotides that are complementary to miRlOb in A172 cells after 24 (FIG. 10A), 48 (FIG. 10B), and 72 hrs.
Figure 10B:
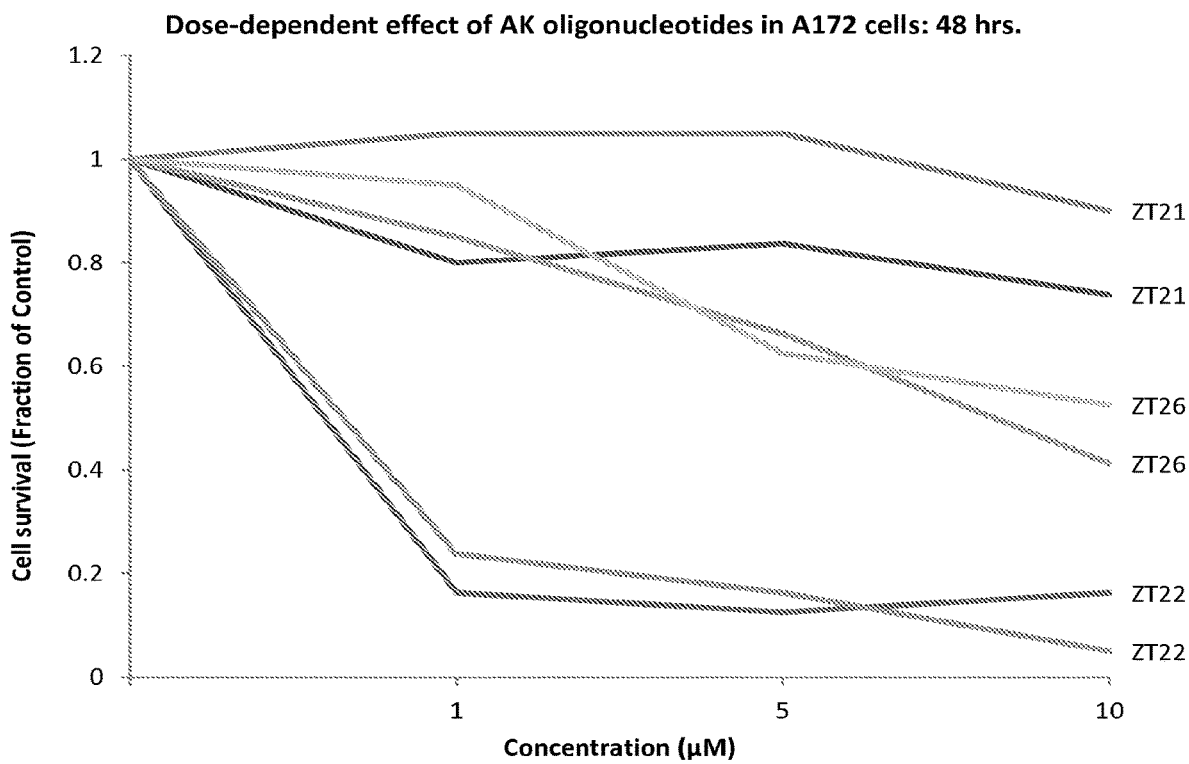
Figure 10C:
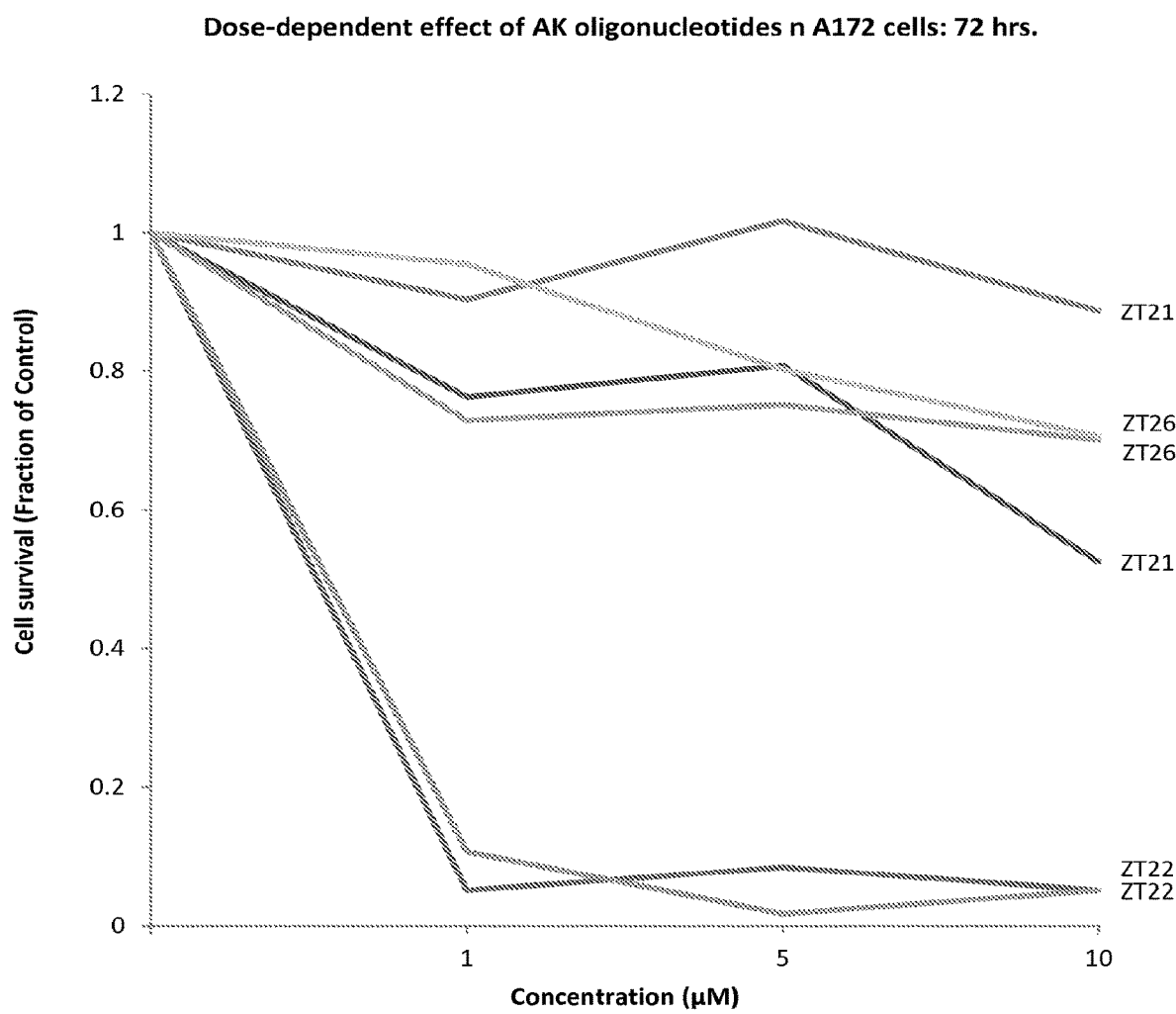

Example 20: Inhibition of Cell Growth by Targeting MIR10B in A172 Glioma Cells The dose-dependent effect of oligonucleotide on A172 cells were investigated with thiophosphonate oligonucleotide, ZT21 (control, contains no neutralizing moieties), ZT22 (contains 4 neutralizing moieties, 55% negative charge reduction), and ZT26 (contains 2 neutralizing moieties, 27% negative charge reduction) complementary to miR10b. miR10b is heavily presented in the glioblastoma cells and play crucial role in their uncontrolled proliferation. Cells were seeded in 24-well plates and, after overnight incubation, regular growth medium was replaced with DMEM/5% FBS supplemented with oligonucleotide at concentrations of 1, 5, and 101.1 M. Cell behavior was observed daily using phase contrast microscopy. Dose-dependent effect on cell growth is illustrated in FIGS. 10A-10C. The labels correspond to the oligonucleotide tested: ZT21 (with no neutralizing moieties), ZT26 (with 2 neutralizing moieties), and ZT22 (with 4 neutralizing moieties). Close to quantitative inhibition of the cell growth was observed for ZT22 oligonucleotide at concentration as low as 1 μM. No effect of ZT22 on miROb-independent HeLa cells was detected.

Example 21: Solubility

Solubility of numerous oligonucleotides from Table 1 in PBS were evaluated by measuring the UV absorption of the solutions at different concentrations of several compounds. All compounds, including highly neutralized ones (ZT7, ZT1, and ZT27 from Table 1), were completely soluble at up to 1 mM concentrations.

Those having ordinary skill in the art will appreciate that various changes can be made to the above exemplary embodiments without departing from the scope of the invention.

---

What is claimed:

1. A compound having structure (III):

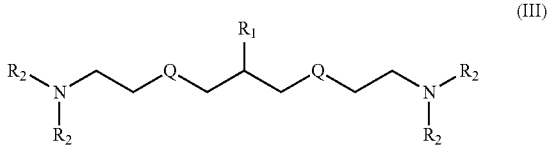

(III)

wherein $R_1$ is a nucleic acid moiety, optionally connected through a spacer group selected from the group consisting of $CH_2OCH_2$, $CH_2SCH_2$, $CH_2$, $CH_2CH_2$ and $CH_2CH_2CH_2$;

the nucleic acid moiety having structure (II)

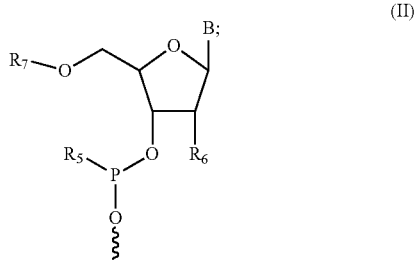

(II)

wherein $R_5$ is $N(CH(CH_3)_2)_2$, wherein $R_6$ is selected from the group consisting of protected OH, protected SH, protected $NH_2$, H, $OCH_3$, $OCH_2CH_3$, F, Cl, $N_3$, $OCH_2OCH_3$, $OCH_2OCH_2CH_3$, $SCH_3$, and $N(CH_3)_2$, wherein $R_7$ is a 5' protecting group selected from the group consisting of dimethoxytrityl (DMTr), monomethoxytrityl (MMTr), and trityl (Tr), and wherein B is a 9-purinyl or a 1-pyrimidinyl nitrogenous base, wherein amino groups are protected with a protecting group;

wherein $R_2$ is, independently for each occurrence, selected from the group consisting of $CH_3$, $CH_2CH_3$, an alkyl, a branched chain alkyl, formyl, acetyl, $CF_3$, trifluoroacetyl, allyl, triphenylmethyl, tert-butyloxycarbonyl, phenoxyacetyl, (4-isopropyl-phenoxy)acetyl, and benzoyl; and wherein Q is, independently for each occurrence, selected from the group consisting of O, S, $OCH_2$, and $CH_2$;

or a pharmaceutically acceptable salt thereof.

2. The compound of claim 1, wherein each $R_2$ is $CH_3$.

3. The compound of claim 1, wherein the 5' protecting group is dimethoxytrityl (DMTr).

4. The compound of claim 1, wherein the 9-purinyl or 1-pyrimidinyl nitrogenous base is selected from the group consisting of 9-adeninyl, 9-guaninyl, 1-cytosinyl, 1-thyminyl, 1-uracilyl, 5-methyl-l-cytosinyl, 7-methyl-9-guaninyl, 5,6-dihydro-l-uracilyl, and 5 hydroxymethyl-l-cytosinyl, and wherein amino groups of the nitrogenous base are protected with a protecting group.

5. The compound of claim 1, wherein the nitrogenous base comprises a protecting group, wherein the protecting group is selected from the group consisting of phenoxyacetyl, (4-isopropyl-phenoxy)acetyl, benzoyl, and acetyl.

6. An oligonucleotide comprising:
   from 5 to 500 nucleotides; and
   at least one neutralizing moiety covalently bonded to a phosphate of the oligonucleotide sugar-phosphate backbone, optionally through a spacer group selected from the group consisting of $CH_2OCH_2$, $CH_2SCH_2$, $CH_2$, $CH_2CH_2$ and $CH_2CH_2CH_2$;
   wherein the at least one neutralizing moiety has structure (III):

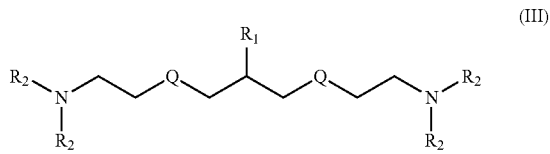

(III)

wherein $R_1$ is the point of attachment to the oligonucleotide or spacer group;

$R_2$ is, independently for each occurrence, selected from the group consisting of $CH_3$, $CH_2CH_3$, an alkyl, a branched chain alkyl, formyl, acetyl, $CF_3$, trifluoroacetyl, allyl, triphenylmethyl, tert-butyloxycarbonyl, phenoxyacetyl, (4-isopropyl-phenoxy)acetyl, and benzoyl; and Q is, independently for each occurrence, selected from the group consisting of O, S, $OCH_2$, and $CH_2$.

7. The oligonucleotide of claim 6, wherein the oligonucleotide is a single stranded or a double stranded oligonucleotide.

8. The oligonucleotide of claim 7, wherein the oligonucleotide is an oligodeoxyribonucleotide or an oligoribonucleotide.

9. The oligonucleotide of claim 6, wherein the oligonucleotide comprises about 1 to about 500 neutralizing moieties.

10. The oligonucleotide of claim 7, wherein the oligonucleotide comprises one or more modified nucleotides and/or synthetic nucleotides comprising one or more of:
   (i) a modified nitrogeneous base selected from the group consisting of 5-methylcytosine, dihydrouridine, 7-methylguanosine, 7-methylguanine, 5,6 dihydrouracil 5,6-dihydro-l-uracilyl, and 5 hydroxymethyl-l-cytosinyl;
   (ii) a modified pentose sugar selected from the group consisting of 2'-$OCH_3$ ribose and 2'-fluoro deoxyribose; and
   (iii) a modified phosphate selected from the group consisting of $PSO_3"$, $PS_2O_2"$, $PO_4CH_3$ and $PSO_3CH_3$.

* * * * *

SEQUENCE LISTING

<160> NUMBER OF SEQ ID NOS: 31

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
atagtagtag tcctagtct                                                  19

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
atagtagtag tcctagtct                                                  19

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
atagtagtag tcctagtct					19

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
uucguaguug ucuuagucc					19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
uucguaguug ucuuagucc					19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
uucguaguug ucuuagucc					19

<210> SEQ ID NO 7
<211> LENGTH: 19
<212> TYPE: RNA
<213> ORGANISM: Artificial Sequence
<220> FEATURE:
<223> OTHER INFORMATION: Synthetic

<400> SEQUENCE: 7
uucguaguug ucuuagucc					19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
uucguaguug ucuuagucc					19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
uucguaguug ucuuagucc					19

<210> SEQ ID NO 10
<211> LENGTH: 19
<212> TYPE: RNA

<213> ORGANISM: Artificial Sequence
<220> FEATURE:
<223> OTHER INFORMATION: Synthetic

<400> SEQUENCE: 10
uucguaguug ucuuagucc                                            19

<210> SEQ ID NO 11
<211> LENGTH: 21
<212> TYPE: RNA
<213> ORGANISM: Artificial Sequence
<220> FEATURE:
<223> OTHER INFORMATION: Synthetic

<400> SEQUENCE: 11
ucguacuuau cuuaauccua c                                         21

<210> SEQ ID NO 12
<211> LENGTH: 21
<212> TYPE: RNA
<213> ORGANISM: Artificial Sequence
<220> FEATURE:
<223> OTHER INFORMATION: Synthetic

<400> SEQUENCE: 12
ucguacuuau cuuaauccua c                                         21

<210> SEQ ID NO 13
<211> LENGTH: 21
<212> TYPE: RNA
<213> ORGANISM: Artificial Sequence
<220> FEATURE:
<223> OTHER INFORMATION: Synthetic

<400> SEQUENCE: 13
ucguacuuau cuuaauccua c                                         21

<210> SEQ ID NO 14
<211> LENGTH: 21
<212> TYPE: RNA
<213> ORGANISM: Artificial Sequence
<220> FEATURE:
<223> OTHER INFORMATION: Synthetic

<400> SEQUENCE: 14
ucguacuuau cuuaauccua c                                         21

<210> SEQ ID NO 15
<211> LENGTH: 21
<212> TYPE: RNA
<213> ORGANISM: Artificial Sequence
<220> FEATURE:
<223> OTHER INFORMATION: Synthetic

<400> SEQUENCE: 15
ucguacuuau cuuaauccua c                                         21

<210> SEQ ID NO 16
<211> LENGTH: 21
<212> TYPE: RNA
<213> ORGANISM: Artificial Sequence
<220> FEATURE:
<223> OTHER INFORMATION: Synthetic

<400> SEQUENCE: 16
gcguaggauu aagauaagua c                                         21

<210> SEQ ID NO 17
<211> LENGTH: 21
<212> TYPE: RNA
<213> ORGANISM: Artificial Sequence
<220> FEATURE:
<223> OTHER INFORMATION: Synthetic

<400> SEQUENCE: 17
ucguacuuau cuuaauccua c                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetic

<400> SEQUENCE: 18
ucguacuuau cuuaauccua c                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetic

<400> SEQUENCE: 19
ucguacuuau cuuaauccua c                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic

<400> SEQUENCE: 20
ucguacuuau cuuaauccua c                                              21

<210> SEQ ID NO 21
<211> LENGTH: 23
<212> TYPE: RNA
<213> ORGANISM: Artificial Sequence
<220> FEATURE:
<223> OTHER INFORMATION: Synthetic

<400> SEQUENCE: 21
cacaaaaucg guucuacagg gua                                            23

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
cacaaaaucg gutcuacagg gua                                            23

<210> SEQ ID NO 23
<211> LENGTH: 13
<212> TYPE: RNA
<213> ORGANISM: Artificial Sequence
<220> FEATURE:

```
<223> OTHER INFORMATION: Synthetic

<400> SEQUENCE: 23
cuguggaagu cua                                                          13

<210> SEQ ID NO 24
<211> LENGTH: 13
<212> TYPE: RNA
<213> ORGANISM: Artificial Sequence
<220> FEATURE:
<223> OTHER INFORMATION: Synthetic

<400> SEQUENCE: 24
cuguggaagu cua                                                          13

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
agactaggac tactactatt                                                   20

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
cacaaaaucg gutcuacagg gua                                               23

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
atagtagtag tcctagtct                                                    19

<210> SEQ ID NO 28
<211> LENGTH: 23
<212> TYPE: RNA
<213> ORGANISM: Artificial Sequence
<220> FEATURE:
<223> OTHER INFORMATION: Synthetic

<400> SEQUENCE: 28
cacaaaaucg guucuacagg gua                                               23

<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29
cacaaaaucg gutcuacagg gua                                               23
```

```
<210> SEQ ID NO 30
<211> LENGTH: 19
<212> TYPE: RNA
<213> ORGANISM: Artificial Sequence
<220> FEATURE:
<223> OTHER INFORMATION: Synthetic

<400> SEQUENCE: 30
uucguaguug ucuuagucc                                              19

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
atagtagtag tcctagtct                                              19
```